(12) United States Patent
Bennett et al.

(10) Patent No.: US 11,963,901 B2
(45) Date of Patent: Apr. 23, 2024

(54) APPARATUS AND METHOD OF TREATING AN APPROACHING PHYSIOLOGICAL EVENT AND INCREASING AN INTENSITY OF THE EVENT

(71) Applicants: Jeffrey Bennett, Maple Grove, MN (US); Shawn McCutcheon, White Bear Lake, MN (US); Michael F. Hoey, Maple Grove, MN (US); Rachel Goldstein, Houston, TX (US); Dicken S. C. Ko, Weston, MA (US)

(72) Inventors: Jeffrey Bennett, Maple Grove, MN (US); Shawn McCutcheon, White Bear Lake, MN (US); Michael F. Hoey, Maple Grove, MN (US); Rachel Goldstein, Houston, TX (US); Dicken S. C. Ko, Weston, MA (US)

(*) Notice: Subject to any disclaimer, the term of this patent is extended or adjusted under 35 U.S.C. 154(b) by 0 days.

(21) Appl. No.: 17/789,480

(22) PCT Filed: Dec. 28, 2020

(86) PCT No.: PCT/US2020/067234
§ 371 (c)(1),
(2) Date: Jun. 27, 2022

(87) PCT Pub. No.: WO2021/134085
PCT Pub. Date: Jul. 1, 2021

(65) Prior Publication Data
US 2023/0042557 A1  Feb. 9, 2023

Related U.S. Application Data

(60) Provisional application No. 63/048,630, filed on Jul. 6, 2020, provisional application No. 62/954,434, filed on Dec. 28, 2019.

(51) Int. Cl.
*A61F 5/41* (2006.01)
*A61N 1/04* (2006.01)
*A61N 1/36* (2006.01)

(52) U.S. Cl.
CPC .............. *A61F 5/41* (2013.01); *A61N 1/0456* (2013.01); *A61N 1/0492* (2013.01); *A61N 1/36034* (2017.08); *A61F 2005/418* (2013.01)

(58) Field of Classification Search
CPC ......... A61F 5/41; A61F 2005/411–418; A61H 19/00–50; A61H 21/00; A61N 1/0456; A61N 1/0484; A61N 1/0492
See application file for complete search history.

(56) References Cited

U.S. PATENT DOCUMENTS

| 5,385,577 A | 1/1995 | Maurer et al. |
| 5,487,759 A | 1/1996 | Bastyr et al. |

(Continued)

FOREIGN PATENT DOCUMENTS

| JP | 2013500080 A | 1/2013 |
| WO | 2012040243 A1 | 3/2012 |

(Continued)

OTHER PUBLICATIONS

The International Search Report and Written Opinion rendered by the International Searching Authority for PCT/US2020/67234, dated Jul. 1, 2021, 6 pages.

(Continued)

*Primary Examiner* — Thaddeus B Cox
(74) *Attorney, Agent, or Firm* — Skaar Ulbrich Macari, PA

(57) ABSTRACT

A flexible neuromodulation device and method capable of varying a neuromodulation therapy in order to prevent, delay, or control a sexual emission, and/or increasing an intensity of a sexual climax.

20 Claims, 32 Drawing Sheets

(56) References Cited

U.S. PATENT DOCUMENTS

| | | |
|---|---|---|
| 6,334,859 B1 | 1/2002 | Richter |
| 6,907,293 B2 | 6/2005 | Grill et al. |
| 7,527,589 B2 | 5/2009 | Squicciarini |
| 8,509,900 B2 | 8/2013 | Boyd et al. |
| 9,358,383 B2 | 6/2016 | Boyd et al. |
| 9,364,667 B1 | 6/2016 | Dinsmoor et al. |
| 9,757,584 B2 | 9/2017 | Burnett |
| 9,974,593 B2 | 5/2018 | Barman |
| 10,016,600 B2 | 7/2018 | Creasey et al. |
| 10,322,282 B2 | 6/2019 | Wei et al. |
| 10,543,382 B2 | 1/2020 | Rockweiler et al. |
| 10,773,072 B2 | 9/2020 | Gollan |
| 11,224,742 B2 | 1/2022 | Burnett |
| 2002/0055702 A1 | 5/2002 | Atala et al. |
| 2009/0054950 A1 | 2/2009 | Stephens |
| 2010/0160712 A1 | 6/2010 | Burnett et al. |
| 2018/0110974 A1 | 4/2018 | Deer |
| 2018/0111010 A1 | 4/2018 | Kuo |
| 2018/0184939 A1* | 7/2018 | Christiansen ........ A61B 5/6833 |
| 2018/0200514 A1 | 7/2018 | Druke et al. |
| 2018/0345003 A1 | 12/2018 | Gollan |
| 2019/0381310 A1* | 12/2019 | Willand ............... A61N 1/0492 |
| 2021/0137777 A1 | 5/2021 | Bennet et al. |
| 2021/0268278 A1 | 9/2021 | Agahari |
| 2021/0361941 A1* | 11/2021 | Gollan ................. A61N 1/0456 |
| 2022/0105342 A1 | 4/2022 | Bennet et al. |

FOREIGN PATENT DOCUMENTS

| | | |
|---|---|---|
| WO | 2014151431 A2 | 9/2014 |
| WO | 2019/130311 A1 | 7/2019 |
| WO | 2020/146802 A1 | 7/2020 |
| WO | 2021134085 A1 | 7/2021 |

OTHER PUBLICATIONS

Creative Mechanisms Staff, Everything You Need to Know About Living Hinges (Design, Prototypes, and Manufacturing), dated May 13, 2016, published at https://www.creativemechanisms.com/blog/everything-you-need-to-know-about-living-hinges.

Sunny Sahota, How to Design Living Hinges, Mechanical Design Tips, dated Nov. 14, 2015, published at https://www.fictiv.com/articles/how-to-design-living-hinges.

* cited by examiner

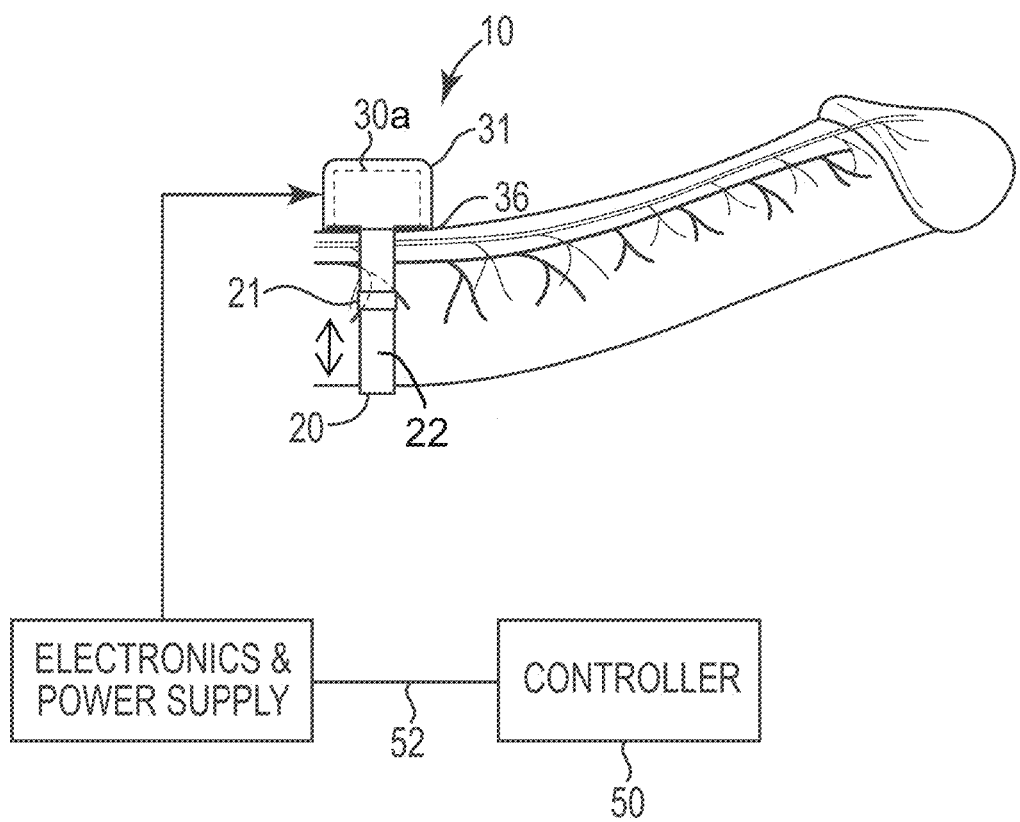
FIG. 1
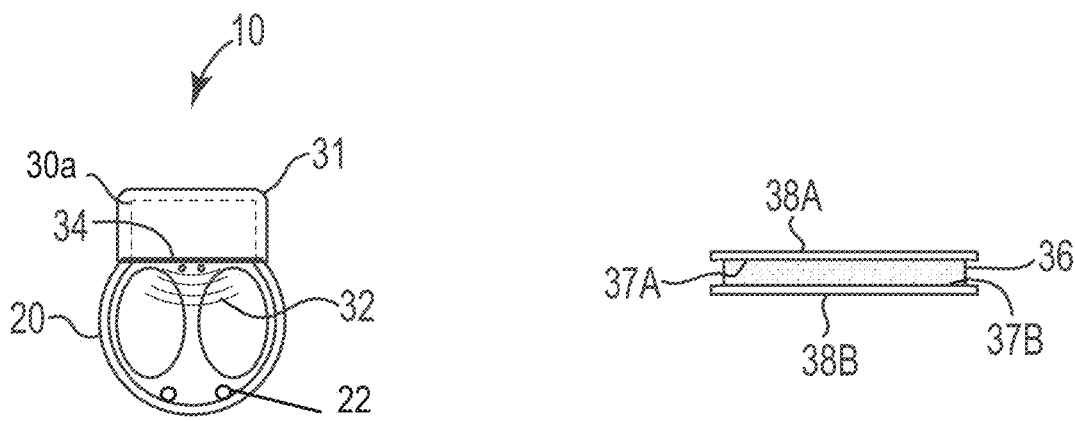
FIG. 2
FIG. 3

APPARATUS AND METHOD OF TREATING AN APPROACHING PHYSIOLOGICAL EVENT AND INCREASING AN INTENSITY OF THE EVENT

PRIORITY

This Application is a Section 371 US National Stage Application of PCT Application No. PCT/US20/67234, filed Dec. 28, 2020, which claims priority to and the benefit of U.S. Provisional Patent Application No. 62/954,434, filed Dec. 28, 2019, and U.S. Provisional Patent Application No. 62/048,630, filed Jul. 6, 2020; with each of the identified applications and disclosures being incorporated fully herein by reference.

FIELD

The present invention relates generally to the treatment or modification of pelvic health functions or conditions. For example, treatment or modification of a sexual dysfunction, such as premature ejaculation in a male or a lack of or non-stopping of an orgasm in a female. In these embodiments the present invention includes an apparatus and method for accelerating, delaying, ceasing, or stopping an approaching premature ejaculation or orgasmic event. The present invention is also able to increase an intensity of an orgasm upon occurrence.

BACKGROUND

A number of devices and methods are available for enabling those with a sexual dysfunction, such as premature ejaculation, to delay an ejaculatory event. These devices and methods are generally either applied to the surface of the penis, in the form of a pharmacological cream, or are implanted within or proximate to the penis in order to deliver an electrical pulse to a nerve of the penis.

Generally speaking, the methods that are available, or which have been described, include the use of various constriction devices. These devices, like the one described in U.S. Pat. No. 5,921,914 have been used for centuries and are typically applied around a base of a penis to constrict it. The constriction causes the penis to stay erect and prevents the flow of semen. The problem with these constriction devices is that blood is prevented from flowing out of the penis. This permits a blood pooling effect that can causes the temperature of the penis to drop, thereby causing it to feel cold. This can be unpleasant for the person suffering from premature ejaculation and their sexual partner.

In order to overcome the shortcomings of the constriction devices, various compounds were developed to treat premature ejaculation. These compounds have traditionally taken the form of topical anesthetic compounds. The problem with topical compounds is that they are typically applied shortly before a sexual encounter. The application of the topical compound in proximity to a sexual encounter has often resulted in a transfer of the topical compound to a sexual partner. As a result, the partner of an individual suffering from premature ejaculation can be exposed to the compound, thereby desensitizing their sexual organs and delaying or negatively impacting their sexual experience. As such, topical compounds have failed to provide an effective solution to individuals suffering from premature ejaculation.

In order to counter the problems associated with topical compounds, patients have been prescribed antidepressants as a form of treatment. The use of antidepressants has been widely disclosed, including in U.S. Pat. Nos. 4,507,323, 4,940,731, 5,151,448, and 5,276,042. These drugs have had some success; however, their efficacy tends to decrease over time, and they are plagued with serious side effects that can cause patients to stop using the drugs.

When topical compounds and drugs failed to provide an adequate solution, medical device companies developed various electrical stimulation devices that stimulate the nerves of the penis in an attempt to prevent premature ejaculation. For instance, in U.S. Pat. No. 7,328,069 to Gerber, Medtronic developed a device that is implantable into an abdomen of a patient, with leads extending into a patient's pelvic cavity to stimulate the pudendal nerve. The problem with these implantable devices is that they carry the shortcomings of all the complications associated with surgery, including, but not limited to, infection. Others developed electrical stimulation devices that did not have to be implanted but would instead be placed over the penis. These devices, like the one described in U.S. Pat. No. 9,017,244 to Chiu, use cuffs or condom-shaped devices that deliver electrical stimulation to the penis.

Despite all of the devices available or described, a need remains for an improved device and method for treating sexual dysfunction. A device and method of treating a sexual dysfunction, such as premature or delayed ejaculation, is needed that doesn't negatively impact the experience of both the sufferer and partner, and that does not require implantation. Additionally, a device and method of treatment that senses an anatomical approaching ejaculatory or orgasm event and then applies a therapy to stop the event would also be very desirable. Still further, a device and method of treatment that senses an anatomical approaching ejaculatory or orgasm event and then applying a therapy to stop or control the event while also intensifying the event upon occurrence would also be very desirable.

There is also a need for a device that is able to increase the intensity of an orgasm by stimulation of muscles, nerves, or both without the need to insert a stimulation device into a cavity of a user. The ability to increase the intensity of an orgasm, with or without other listed benefits disclosed herein, is needed for patients or users that experience a decrease in the intensity of an orgasm due to any number of conditions. There is also a need for a device and method of treating premature or delayed orgasm for women. Similarly, there is a need for a device and therapy that can increase the intensity of a female orgasm without the need of prescription drugs or implantable devices.

SUMMARY

The present invention is a treatment for pelvic health dysfunctions or sexual dysfunctions, such as, for example, premature or delayed ejaculation or orgasm, which are conditions impacting up to 30% of men and women worldwide. The present invention is also able to increase the intensity of an ejaculation or orgasm. As men and women age their hormone levels begin to decrease. The decreasing hormone levels can negatively impact their ejaculation and orgasms. Additionally, various lifestyle choices or injuries can also negatively impact the times and intensity of ejaculations and orgasms.

Various embodiments of the present invention are configured to sense anatomical physiological changes, such as an approaching ejaculatory event, and then apply a therapy to transdermally stimulate or confuse nerves (e.g., the pudendal nerve) or muscles to stop, cease, increase, or change an anatomical physiological event, such as an ejaculatory or orgasm event. For the control of ejaculation or orgasm, the devices and methods described herein stimulate, and thus inhibit or promote depending upon the desired effect, the nerve pathway between the penis or vagina and the brain. The devices or methods can be adjusted in order to delay or increase the time to and/or intensity of an ejaculation or orgasm. The devices and methods include the ability of a male or female being able to control the timing and/or intensity of the ejaculation or orgasm. The entire neural pathway or a portion thereof may be stimulated or treated to impart the desired therapy provided herein.

In one example embodiment of the invention, a cuff, ring, patch, clip, or similar type of device is removably secured to a portion of the penis, or to another anatomical location effective to treating a condition such as premature ejaculation. The device may be secured to a portion of the penis or the perineum, or another anatomical location to deliver the treatment or therapy. Various devices can include one or more sensors that are capable of sensing an anatomical event, such as an approaching ejaculatory or orgasm event or other events, such as a sneeze, that may cause incontinence. The sensors are capable of detecting any type of physiological, chemical, or electrical phenomenon related to the anatomical event. For example, the sensors can be configured to detect an increase or change in the girth of the penis, the state of an electrical potential generated by the penis or vagina, a change in temperature of a penis, vagina, or surrounding skin.

The devices and methods are able to utilize the detected physiological, chemical, or electrical phenomenon to control the application of the therapy. In one embodiment of the invention, the therapy may consist of a pulsating constriction cuff that is capable of mechanically stimulating the pudendal nerve to cause "ultra" nerve confusion. The cuff can include inner inflatable members that can be inflated and deflated to compress the penis. The cuff can also include a bimetal inner ring or surface that is able to compress the penis and its nerves upon application of an electric current to the devices.

The therapy devices may include a cuff that is able to deliver a pharmaceutical compound that is able to desensitize the pudendal nerve or dorsal nerve. The cuff is able to apply the compound to the penis or anatomical location and then act as a barrier to a sexual partner to prevent cross exposure. The cuff may also use any of the described embodiments to apply the compound and then to apply pressure to the penis in order to more effectively transmit the compound through the dermis and to the nerve.

The cuff or a similar support device can also comprise a wave producing mechanism generated by an ultrasound source, such as a crystal, to create waves that interfere with various nerves of the penis or vagina or assist in transmitting the compound through the dermis. The waves are transmitted at a frequency that interferes with the signal pathway, thus delaying or accelerating an ejaculatory or orgasm event. In another example embodiment of the invention, the cuff may comprise other elements (e.g., electrical, mechanical, chemical or magnetic) that when activated would also interfere with or promote nerve signals from the penis to delay or accelerate an ejaculation.

For women, the devices and therapies comprise cups, patches, vaginal inserts and the like that are able to sense physiological changes in the vagina or surrounding area and then able to apply a therapy to either delay, accelerate, or intensify an orgasm.

The present invention may also include a remote wired or wireless controller that controls the delivery of the treatment. For example, the controller can be activated via a dedicated device or a smartphone, watch, or similar device that someone would wear or hold. Anyone having control of the controller would be able to activate or deactivate the therapy device, such as a cuff, cup, ring, patch or other support structure. When deactivated, the therapy device would not interfere or interact with nerve signals transmitted between the anatomy and physiological event to be treated or modified. When activated, however, the therapy device would cause ultra nerve confusion and prevent or modify an ejaculatory or orgasm event. The level of nerve signal confusion may be controlled by the person holding or wearing the controller so that the timing of a desired ejaculation or orgasm can be controlled by either party.

In other embodiments of the present invention, a foldable or hingeable stimulation device, such as a patch, can include a housing, a circuit board element, one or more electrodes or pairs of electrodes, and a power supply (e.g., battery). Further, a touch button or other actuation mechanism can be included. The actuation mechanism can be pressed to turn the device on and off, pressed or tapped to increase or vary stimulation, and the like. This device provides non-uniform and changing effective electrical stimulation timing of pulses with varying effective frequencies to "confuse" nerves and receptors involved in the ejaculatory or orgasm process. The device is hingeable at living hinge portions such that the device can be selectively manipulated and placed with the electrodes contacting the tissue for stimulation. The device can be placed on the genitals, transperineally, or inserted at least partially into a vaginal cavity with one or more electrodes crossing the plane of nerves. For instance, the nerves running parallel with the urethra.

In yet other embodiments of the invention, the device includes a design whereby one or more electrodes are positioned near nerves enervating the perineal region. One such set of nerves is the Inferior rectal nerves, which include the inferior hemorrhoidal nerve. These nerves branch from the pudendal nerve, which enervates the prostate. As these nerves and other nerves in the area are stimulated by the device described herein, an intensification of ejaculation can occur once it happens.

The above summary is not intended to limit the scope of the invention, or describe each embodiment, aspect, implementation, feature or advantage of the invention. The detailed technology and preferred embodiments for the subject invention are described in the following paragraphs accompanying the appended drawings for people skilled in this field to well appreciate the features of the claimed invention. It is understood that the features mentioned hereinbefore and those to be commented on hereinafter may be used not only in the specified combinations, but also in other combinations or in isolation, without departing from the scope of the present invention.

BRIEF DESCRIPTION OF THE DRAWINGS

FIG. 1 is a perspective view of the sexual dysfunction treatment system, according to embodiments of the present invention.

FIG. 2 is an end view of the sexual dysfunction treatment system according to embodiments of the present invention.

FIG. 3 is a cross-sectional view of a coupling member used with a transducer, according to embodiments of the present invention.

DETAILED DESCRIPTION

Figure 4:
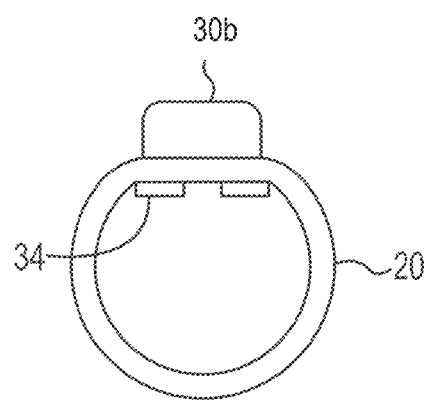
FIG. 4 is an end view of a sexual dysfunction treatment system with an elastic ring or base, according to embodiments of the present invention.

In the following descriptions, the present invention will be explained with reference to various exemplary embodiments. Nevertheless, these embodiments are not intended to limit the present invention to any specific example, environment, application, or particular implementation described herein. Therefore, descriptions of these example embodiments are only provided for purpose of illustration rather than to limit the present invention.

Dimensions and relative proportions of components are merely example embodiments and can be varied unless specifically limited in a given claim. Thus, the dimensions can be varied without departing from the scope of the invention.

The present invention illustrates devices, systems, and methods for treating sexual dysfunctions such as premature or delayed ejaculation and decreased orgasm intensity. While the invention is particularly advantageous for patients suffering from a sexual dysfunction such as premature ejaculation, it may also be used by anyone that desires to delay, alter, or modify their orgasm or climax experience.

The present invention may also be used as a means of desensitizing a sexual organ for the purpose of altering sexual activity or orgasms. The present invention may have application in humans as well as veterinary applications. Although the present invention is described as being applicable to males, it should be appreciated that the disclosed systems, devices, and methods may also be used to treat a female pelvic health disorders, including but not limited to, sexual dysfunction and incontinence.

In example embodiments of the invention, as illustrated in FIGS. 1-14, a device, method or physiological event control system 10 is shown for controlling physiological events, such as the premature emission of an ejaculate. In these embodiments, the device 10 includes a ring, base, or cuff 20 or a patch 60 that is removably positionable about a portion of a penis, to a perineum, or another anatomical location of an individual that desires to alter a physiological event such as sexual function—e.g., delaying, accelerating, altering, or modifying emissions or orgasms.

The device 10 also includes one or more neuromodulation devices, such as an ultrasound generator 30a or an electrical generator 30b, attached to or incorporated as part of the cuff 20 or patch 60. The ultrasound generator 30a or electrical generator 30b generates energy that causes nerve confusion within the pudendal nerve or dorsal nerve of the penis. The nerve confusion causes a change in sexual function (i.e., delay in an ejaculatory event). It should be noted that other neuromodulation devices, such as mechanical stimulation devices, may also be used and should be considered to be within the spirit and scope of the invention.

One of the purposes of the cuff 20 or patch 60 is to position the ultrasound generator 30a or electrical generator 30b proximate to a portion of a sexual organ, such as a penis, vagina, or perineum to be treated. As will be discussed in more detail below, in one embodiment of the present invention, a controller 50 is provided that controls the ultrasound generator 30a, electrical generator 30b, and/or other features of the present invention.

One important feature of some example embodiments of the invention is its ability to sense an approaching ejaculatory or orgasm event and then to apply a therapy. The therapy devices 10 can include one or more sensors 22 that are capable of detecting any type of physiological, chemical, or electrical phenomenon related to the ejaculatory or orgasm event. For example, the sensors 22 are able to detect an increase or change in the girth of the penis, a state of an electrical potential generated by the penis or vagina, and/or a change in temperature of the penis, vagina or surrounding tissue.

As illustrated in FIG. 1, in a ring or cuff 20 embodiment of the present invention, the ring or cuff 20 may extend about a circumference of a patient's penis. In one of the methods of treating or delaying sexual emissions, the ring or cuff 20 may be positioned generally close to a base of the penis. However, the ring or cuff 20 may be placed at or along any location of the sexual organ that may provide effective therapy. It should be noted that the location of effective therapy may be different for different individuals and treatment applications.

The sensor(s) 22 of the ring or cuff 20 may comprise a band that extends about a circumference of the penis. As an ejaculatory or orgasm event approaches, the penis generally changes shape or size. A rate of these changes can increase in time as an ejaculatory or orgasm event grows near. The sensor(s) 22 is able to detect these changes and begin to apply a therapy to cause nerve confusion, and thus delay ejaculation. Conversely, the devices 10 of the present invention is able to apply therapy to accelerate an ejaculatory or orgasm event by stimulating the nerves or muscles to increase excitement.

The ring or cuff 20 may comprise a generally elastomeric material such that it can be stretched over the sexual organ prior to or during use. The ring or cuff 20 may be manufactured from a durable yet supple material such as silicone. As the example device 10 may be worn during intercourse, the ring cuff or 20 should ideally have a profile that is either not noticeable by a partner or is enjoyable to the partner. Lastly, the material of the ring or cuff 20 permits it to be easily cleaned after use.

The ring or cuff 20 may also be adjustable to permit it to be adjusted to accommodate users of various sizes. The ring or cuff 20 may be manufactured with various features that permit it to be adjustable. In an example embodiment, the ring or cuff 20 may have a pair of opposed free ends that may be coupled together by a coupler 21. Other adjustable mechanisms are also possible and the embodiments presented herein should not be considered limiting.

As illustrated in FIG. 2, the ring or cuff 20 is used to support the ultrasound generator 30a or electrical generator 30b, as well as power source. In various examples, the ultrasound generator 30a or electrical generator 30b is non-implantable and configured to generate an ultrasound output or wave 32, or an electrical current in response to an approaching ejaculatory event.

A driving signal is provided by the controller 50 that is in operative communication with the sensor(s) 22. The controller 50 controls the amount of energy emitted and is also able to control a pattern of energy emitted or applied to the sexual organ (penis or vagina) or any nerves or muscles being targeted. The controller 50 may be in communication with the ultrasound generator 30a or electrical generator 30b either wirelessly or by a connection 52.

For an ultrasound generator 30a or electrical generator 30b, ultrasound energy or electrical energy, is applied to the surface of the tissue of the genitals or surrounding area by one or more energy emitting surface or probes 34. As illustrated in FIG. 2, energy emitting surface or probes 34 can be in direct physical contact with the tissue of the penis or sexual organ. In other embodiments, the energy emitting surface 34 can be positioned proximate the tissue of the penis or sexual organ. Although depicted near a superior or top surface of a penis, the probes 34 can be placed in any therapeutically effective location on the cuff 20.

The ultrasound generator 30a or electrical generator 30b is configured to emit energy at frequencies or currents needed to deliver the effective or desired therapy. The controller 50, through the sensors 22, is able to detect if an applied therapy is being effective. For instance, the controller 50 is able to detect if there is a decrease or change in the physiological, chemical, or electrical potential characteristics of the penis or sex organ. If no change is detected, the controller 50 may increase, decrease, or modify the amount of energy being applied to the sex organ.

As particularly illustrated in FIG. 2, the emitted or transmitted energy, regardless of type, may be aligned generally normal with the emitting surface of the probes 34. However, in other example embodiments, emitting elements or probes 34 may be generally aligned at varying angles.

The ultrasound generator 30a or electrical generator 30b may be positioned in a housing 31 made of a durable material such as polyvinyl chloride (PVC), polypropylene (PP), polyethylene (PE), polystyrene (PS) as well as nylon polyethylene terephthalate (PET), polyimide (PA), polycarbonate (PC), acrylonitrile butadiene (ABS), polyetheretherketone (PEEK) and polyurethane (PU), to name a few. The ultrasound generator 30a or electrical generator 30b and its housing are ideally resistant to fluids and can be easily cleaned. The ring or cuff 20 may also be manufactured from a similar or dissimilar material as the housing 31. The housing 31 permits a user to remove the ultrasound generator 30a or electrical generator 30b for the purpose of replacement or repair.

When the ultrasound generator 30a or electrical generator 30b is activated, it emits or transmits energy (wave or current) 32 toward a nerve, for example a dorsal nerve or pudendal nerve, that causes it to be stimulated, inhibited, or otherwise modified. In the present invention, the controller 50 is able to change the transmitted energy such as by modifying the intensity and/or pattern of the energy flowing through the probes 34. The ability to change the intensity and pattern of the energy enables the confusion of the nerves or muscles being targeted. The nerve or muscle confusion prevents the nerve signal, indicating an approaching ejaculatory or orgasm event, from traveling to the brain. In one embodiment of the invention, the controller 50 is able to continuously alter the intensity and pattern to adapt in the event the body adapts to the stimulus and begins to send the nerve signal, indicating an ejaculatory or orgasm event, to the brain.

The ultrasound generator 30a generally consists of a generator that responds to a high-frequency alternating current. The high frequency electric current is then converted by the ultrasound generator 30a into mechanical (acoustic) vibrations. The ultrasound generator 30a consists of a crystal inserted between two electrodes. As an alternating electrical charge is applied to the surfaces of the crystal, the crystal is made to vibrate rapidly, thereby creating sound waves.

In yet another embodiment of the invention, the ultrasound generator 30a can generate an energy wave or vibration through a coupling medium. It is known that ultrasound waves are transmitted more effectively through water, oil, or transmission gel, than through air. Consequently, as illustrated in FIG. 3, a coupling member 36 may be used to "couple" the emitting surface of the probes 34 or the ultrasound generator 30a to the patient's sex organ (e.g., penis or vagina) or the surrounding area in order to ensure that the ultrasound waves are properly transmitted to the desired treatment site. The coupling member 36 may, for example, be in the form of a gel or lotion which is applied to the skin of the patient over the area to be treated. The ultrasound generator 30a may then be positioned on the coupling member 36, and the generator is activated. Ultrasound waves 32 produced at the emitting surface 34 are transmitted through the coupling member 36 into the patient to stimulate the target such as the dorsal nerve or pudendal nerve.

In another example embodiment of the invention, the coupling member 36 may comprise a sheet, pad, or disk of material that is capable of transferring sound waves into the sex organ (e.g., penis or vagina) of the patient. The coupling member 36 may have generally opposed planar surfaces 37A, 37B that permit the planar surfaces to be placed against the skin of the patient's sex organ and the emitting surface 34 of the transducer 30. The planar surfaces 37A, 37B may be covered by a film member 38A, 38B that permit the surfaces of the coupling member 36 to remain free of debris. In embodiments where the coupling member 36 comprises a solid or semi solid material, such as a gel, the films 38A, 38B permit the coupling member 36 to retain its moisture content. These pads or coupling member 36 can be sold together with the transducer or sold separately to permit a user to reuse the system device or system 10.

The properties of the ultrasound generator 30a depend upon its diameter and frequency. For example, a small diameter produces a generally small diameter ultrasound beam. In an example embodiment of the invention, ultrasound frequencies of about 400 khz may be used to stimulate the dorsal nerve or pudendal nerve. A range of ultrasound frequency to include 0.5 to 3 MHz may also be used to treat the nerve. A practitioner may use the controller 50 to select a particular frequency depending upon the dimension of the patient.

In an example embodiment of the invention, the other parameters of the device 10 may comprise:
- a pulse width of 1 msec, and a treatable range of 0.01 to 5,000 msec
- a stimulation frequency of 100 Hz
- an ultrasound treatable range of 0.5 to 3 MHz or 0.5 to 5 MHz
- an acoustic power in a treatable range of 400 W/cm$^2$ to 7,500 W/cm$^2$ Other treatable ranges are possible and may be used to treat various conditions. Therefore, the above-cited ranges should not be considered limiting.

Although the devices 10 of the present invention include the controller 50 that is able to automatically control the therapy provided, it can also be at least partially controlled by a user or partner. For instance, the controller 50 can be used to activate the ultrasound generator 30a or electrical generator 30b or other elements within the ring or cuff 20. The controller 50 can also be used to turn off the ultrasound generator 30a or electrical generator 30b by the person being treated, or their partner. Turning off the ultrasound generator 30a or electrical generator 30b ceases the therapy and allows for or permits an ejaculatory event. By providing at least limited control of the controller 50, a user or their partner is able to alter the sexual function, such as delaying ejaculation, until a desired period of time. This control ensures that both parties are able to achieve the sexual satisfaction that they desire.

The system 10 may include a mobile device (e.g., smartphone or other device) in operative communication with the controller 50 or may act as the controller or control module. However, any other type of control device may be used, including but not limited to wireless smart watches and the like. The device 10 may also use a controller 50 that is dedicated to the ultrasound generator 30a or electrical generator 30b. This dedicated device may be wired or wireless. Independent of the type of controller 50 utilized, it should have the functionality to control (e.g., turn on and off the ultrasound generator 30a or electrical generator 30b, receive feedback, monitor data, log data, control or adjust output, etc.) the device or system 10.

Figure 5:
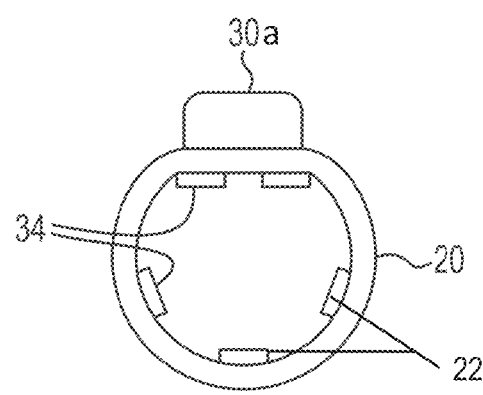
FIG. 5 is an end view of a sexual dysfunction treatment system with an array of transducers, according to embodiments of the present invention.
Figure 6:
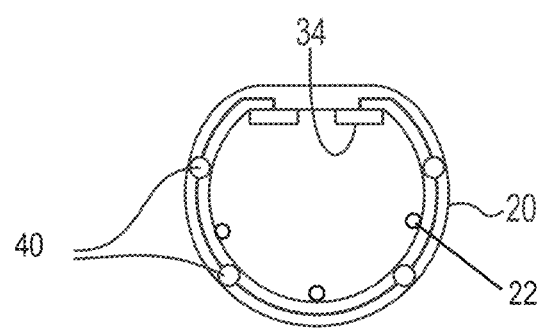
FIG. 6 is a cross-sectional view of a sexual dysfunction treatment system with one or more power supplies embedded within a ring, according to embodiments of the present invention.

As illustrated in FIGS. 4-6, the ring or cuff 20 may incorporate the ultrasound generator 30a or electrical generator 30b, probes 34, other elements (such as power supplies 40) and sensors 22 into its construction so that its profile is minimized. As particularly illustrated in FIG. 4, the probes 34 are positioned proximate the ultrasound generator 30a or electrical generator 30b. In this embodiment, a user uses the position of the housing 31, and thus the probes 34, to correctly position the device or system 10 at a particular therapy location.

In another embodiment of the invention, as illustrated in FIG. 5, the ring or cuff 20 may include a plurality of probes 34 and sensors 22 positioned about the cuff 20. The probes 34 are operatively coupled to the ultrasound generator 30a or electrical generator 30b to emit energy about the circumference of the cuff 20. In this particular embodiment, the probes 34 or sensors 22 may be spaced apart or may be positioned proximate to each other to affect a continuous energy around a circumference of the cuff 20.

As illustrated in FIG. 6, one or more power supplies 40 may be positioned in the ring or cuff 20 to power the ultrasound generator 30a or electrical generator 30b and probes 34. The power supplies 40 and probes 34 may be operatively coupled by an elastic, flexible and/or stretchable conductive material that permits continuous operation of the device or system 10 during adjustment of the cuff 20. In this particular embodiment, the housing 31 may be eliminated and the ultrasound generator 30a or electrical generator 30b incorporated into the cuff 20. The design of this embodiment provides a slimmer profile that may be advantageous for use during a sexual event or encounter. It should be understood that this design may be incorporated into any of the embodiments described herein.

Figure 7:
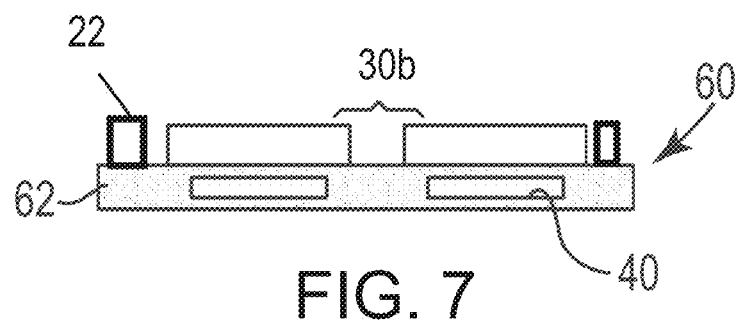
FIG. 7 is an end view of a disposable or reusable sexual dysfunction treatment patch with one or more power supplies and transducers, according to embodiments of the present invention.

As illustrated in FIG. 7, in an example embodiment of the invention, the device 10 may comprise a removable substrate or patch 60 that may be worn by a user to treat a sexual dysfunction, such as premature or delayed sexual ejaculation/orgasm, or to control an intensity of an orgasm/climax.

The patch 60 comprises a base member 62 that can house or support one or more power supplies or sources 40 and an ultrasound generator 30a or electrical generator 30b. The power supplies 40 are operatively coupled to one or more ultrasound generator 30a or electrical generator 30b to generate the therapy signals through the electrodes or probes 34 that can be positioned and removably adhered against a user's tissue to deliver a nerve confusion therapy.

The patch 60, or any other device of the present invention, can include an actuating mechanism that uses the conductive nature of a user's skin to complete a circuit. For instance, once the device 10 is placed on the user the circuit is completed and the device 10 may be activated. When it is activated, the device 10 is able to generate energy for the delivery of a therapy. Once the device 10 is removed, the circuit is broken and the device 10, via the electrodes or probes 34, stop producing energy waves. Other actuating control mechanisms are also contemplated herein and may include an actuation switch that permits a user to turn the device 10 on and off, or otherwise control output of the device 10 as desired. The controller 50, described above, may also be used to control the patch 60.

As with other embodiments of the present invention, the patch 60 also includes one or more sensors 22 that are capable of detecting an approaching ejaculatory event and automatically applying the therapy. In an example embodiment of the invention, the sensors 22 are able to detect and correlate a physiological, chemical, or electrical phenomenon, or change in the penis, vagina, or the perineum, to an approaching ejaculation or orgasm. The controller 50 is then able to regulate the intensity and/or pattern of the energy being delivered to apply the therapy for the desired effect, such as nerve confusion to the targeted nerve or nerves.

Figure 8:
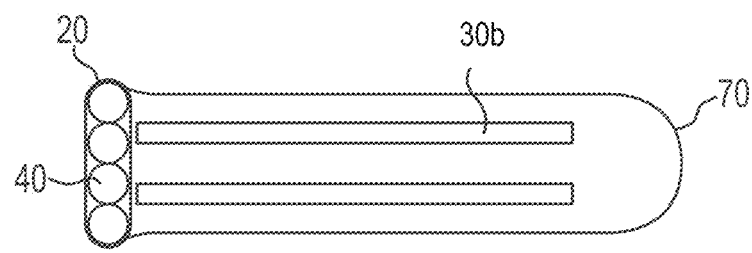
FIGS. 8-9 are side views of sexual dysfunction treatment systems having a sheath, according to embodiments of the present invention.
Figure 9:
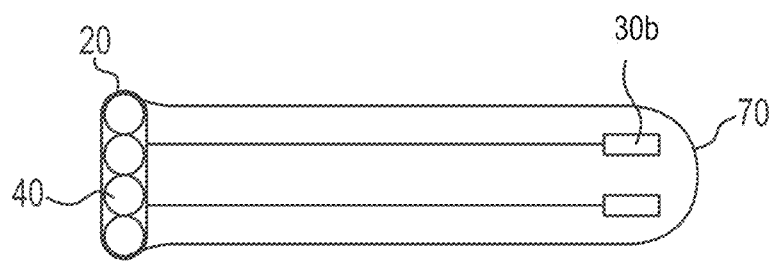

As illustrated in FIGS. 8-9, another embodiment of the present invention incorporates sexual dysfunction treatment with sexually transmitted disease ("STD") prevention. In these particular embodiments, the device or system 10 includes a sheath 70 incorporated with a ring or cuff 20. The sheath 70 includes one or more ultrasound generators 30a or electrical generators 30b that are located in a therapeutic location when worn by a user. The ultrasound generator 30a or electrical generator 30b may be located along a length or circumference of the sheath 70 (as illustrated in FIG. 8) or may be located in a particular location, such as the tip (as illustrated in FIG. 9) or base of the organ. The ultrasound generator 30a or electrical generator 30b may be operatively coupled to one or more power supplies 40 incorporated in the cuff 20. The embodiments of FIGS. 8 and 9 may be worn during a sexual event and then discarded. In another example embodiment, the sheath 70 may be cleaned and reused and the power supplies 40 may be recharged.

As discussed throughout, the cuff 20, patch 60, or sheath 70 may be worn during intercourse. It is also possible, however, that each may be worn during a non-sexual encounter treatment period. For instance, the cuff 20, patch 60, or sheath 70 may be worn under clothing, which permits a user to activate or switch the device 10 into a training mode, whereby a treatment session is activated and nerve confusion is applied to the targeted nerves for the purpose of training the nerves for a desired outcome (e.g., to delay an ejaculatory event or orgasm). The training mode enables a therapy to be applied at any time and at any location. One of the advantages of the present invention is that it is discreet and can be used to deliver therapy prior to a sexual encounter.

Figure 10:
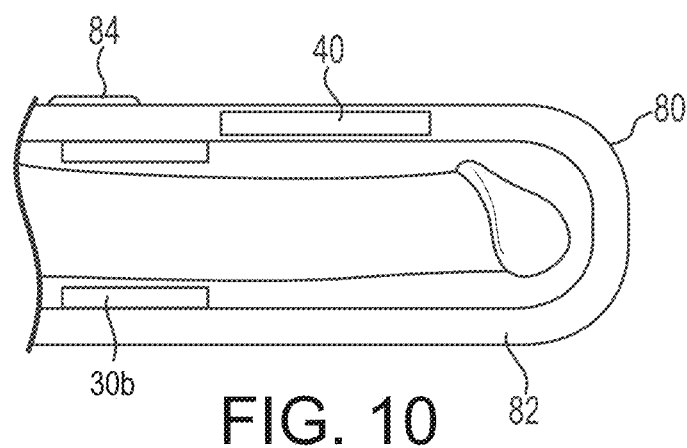
FIG. 10 is a side view of a sexual dysfunction treatment system having a sleeve, according to embodiments of the present invention.

As illustrated in FIG. 10, the device or system 10 of the present invention also includes a reusable therapy sleeve or tube 80 that can be used to administer therapy. The sleeve or tube 80 may be a generally rigid or flexible tube that has a closed end and an open end that is adapted to receive a penis of a user or it can be inserted into a vaginal cavity of a user. The sleeve or tube 80 includes side walls 82 that are able to support one or more ultrasound generators 30*a* or electrical generators 30*b* that are positioned to provide therapy to a user's penis or vaginal wall. The ultrasound generator 30*a* or electrical generator 30*b* may be mounted to an inner or outer surface of the sleeve or tube 80 or may be embedded therein. The sleeve or tube 80 may also include probes or electrodes 34, so as to position the ultrasound generators 30*a* or electrical generators 30*b* a distance from the treatment location.

The side wall 82 of the sleeve or tube 80 is also designed to support one or more power supplies 40 that are operatively coupled to the ultrasound generator 30*a* or electrical generator 30*b*. The power supplies 40 may be recharged by a USB wire or wirelessly. The sleeve or tube 80 may also include a power cord that allows a user to plug in the sleeve or tube 80 to recharge the power supplies 40.

In one example embodiment of the invention, the sleeve or tube 80 may include an actuator 84 to allow a user to control the power flowing to the ultrasound generator 30*a* or electrical generator 30*b*. The actuator 84 can comprise a switch mounted on the sleeve or tube 80 or may comprise a wireless or wired controller 50 in operative communication. As discussed above, the controller 50 may comprise a mobile smart device such as a smartphone, watch, etc.

Figure 11:
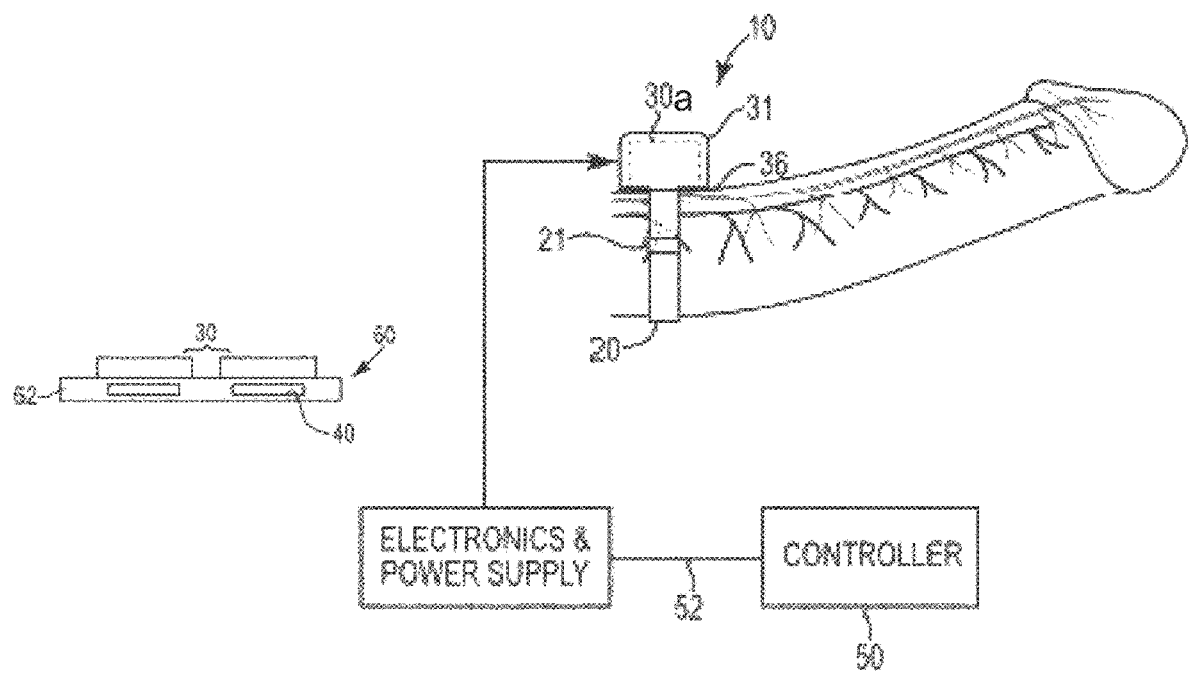
FIG. 11 is a side view of a multi-component sexual dysfunction treatment device, according to embodiments of the present invention.

In another example embodiment of the invention, as illustrated in FIG. 11, a multi-component device or system 10 is employed. In this embodiment, a patch 60 is placed on the on a user (such as on the perineum) to deliver the therapy while the cuff 20 or other sensor 22 is placed in contact with or around the penis to sense the physiological changes in the penis. The cuff 20 or sensor 22 is able to detect the physiological changes and send data to the controller 50, that then controls the patch 60 to deliver the therapy. The controller 50 is able to continuously monitor the cuff 20 or sensor 22 in order to regulate and control the therapy being delivered.

The controller 50 is used to control the energy being delivered (e.g., intensity and/or pattern of energy being applied) for the therapy. The ability to continuously control the intensity and/or pattern of energy being applied enhances the nerve confusion to create an ultra-confusion of nerve stimulation. In a multi-component embodiment (e.g., electrodes on perineum and a band around the penis) the controller 50 is able to sense a change in the girth of the penis and the controller 50 is able to alter the electrical signals sent to the pudendal nerve by the electrodes or probes 34. The opposite is also possible in an embodiment where the band 20 also includes treatment components, such as electrodes or probes 34. While a penis is described as the sexual organ being treated it should be understood that various embodiments of the present invention can be employed to provide a multiple-component therapy to women.

Figure 12:
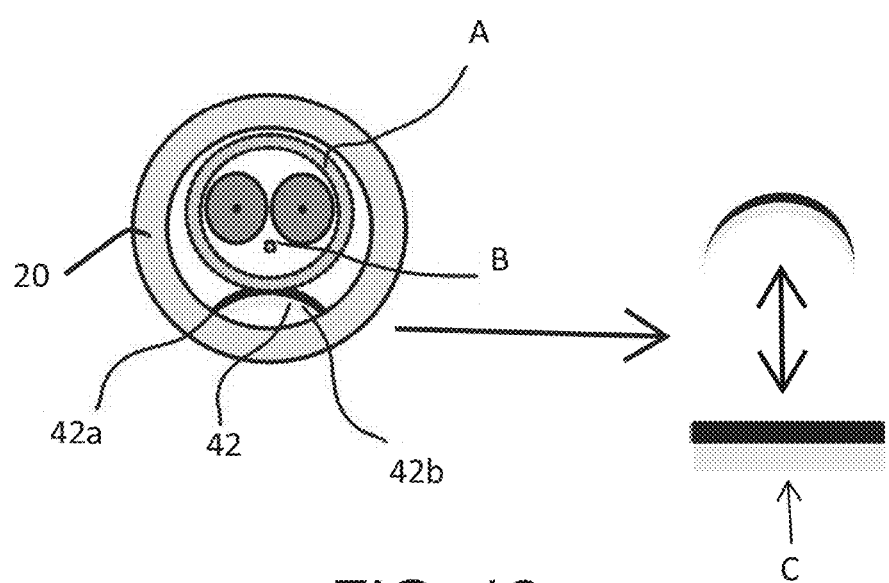
FIG. 12 is a cross-sectional view of a sexual dysfunction treatment system having compressible bimetal inner components in use, according to embodiments of the present invention.

As illustrated in FIG. 12, the cuff 20 may contain bimetal components or interiors 42*a* and 42*b*, such that when a current C is applied it is able to compress or contract, which in turn compresses or contracts the tissue of the penis identified by the letter A. The contractions of the bimetal component 42*a* and 42*b* or interior 42 is used to constrict or contract the muscle and/or nerves of the penis (identified by the letter B) to cause nerve signal propagation. The controller 50 is able to continuously control and change the intensity, duration, and pattern of contractions on the penis or vagina. The variation in the contractions leads to ultra nerve confusion. The mechanical contraction can also be used in conjunction with the patch 60 that is placed on the perineum or other treatment location. The cuff 20 is able to deliver mechanical nerve confusion while the patch 60 provides electrical nerve confusion. The combination of therapies facilitates the delivery of ultra nerve confusion.

Figure 13:
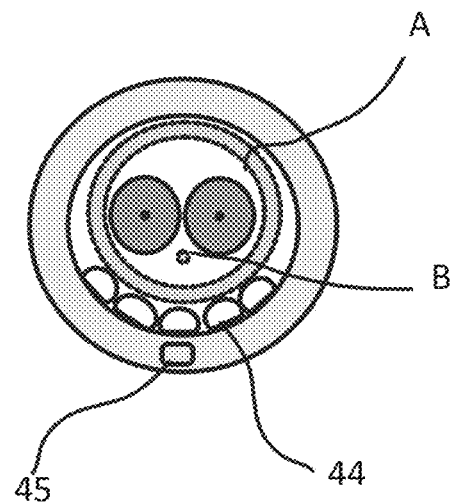
FIG. 13 is a cross-sectional view of a sexual dysfunction treatment system having inner bladders in use, according to embodiments of the present invention.

As illustrated in FIG. 13, other mechanical compressive devices may also be used. For example, the cuff 20 may contain one or more inner bladders 44 that are inflatable and able to compress a portion of the penis A to cause mechanical nerve confusion. The inflatable bladders 44 are in fluid communication with a pump 45 that is controlled by the controller 50. The controller 50 is able to selectively inflate some or all of the inflatable bladders 44. The controller 50 is also able to control the inflation amount or intensity of the bladders 44. By controlling the intensity and the desired number and locations of the bladders 44, the controller 50 is able to apply ultra nerve confusion to the targeted nerves. The cuff 20 with the inflatable bladders 44 may also be used in conjunction with the patch 60.

Figure 14:
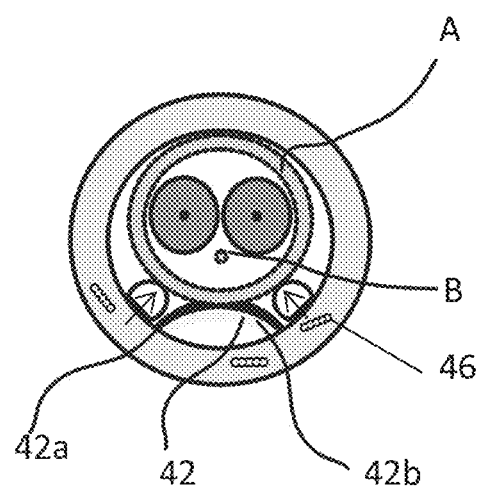
FIG. 14 is a cross-sectional view of a sexual dysfunction treatment system having a desensitizing agent/compound in an inner chamber in use, according to embodiments of the present invention.

As illustrated in FIG. 14, a desensitizing agent/compound 46 can be used in conjunction with the device 10 of the present invention to provided additional nerve blocking properties and further delay an ejaculatory or orgasm event. The desensitizing agent/compound 46 can be applied to the dermis of the penis A, vagina, perineum, or other location and then the device 10 can be activated to exert pressure or an electrical charge to the dermis to assist in penetration of the desensitizing agent/compound 46 into the desired location (e.g., penis). In another embodiment, the desensitizing agent/compound 46 can be stored in an interior of the cuff 20 and delivered through openings onto the skin or dermis of the penis A being treated. Controller 50 is in operative communication with a pump 45 or other like device that is used to deliver the desensitizing agent/compound. The desensitizing agent/compound 46 can also be used with the patch 60. Once a desensitizing agent/compound 46 has been administered, the cuff 20 or patch 60 can be removed without concern for cross exposure to a partner.

In yet another embodiment of the present invention, controller 50 is able to control the delivery of a therapy based upon sensing a physiological state or action of a partner. For instance, if a partner increases the movement or intensity associated with intercourse, the controller 50 is able to control the cuff 20, patch 60, or a combination, to activate to delay an ejaculatory or orgasm event.

Figure 15:
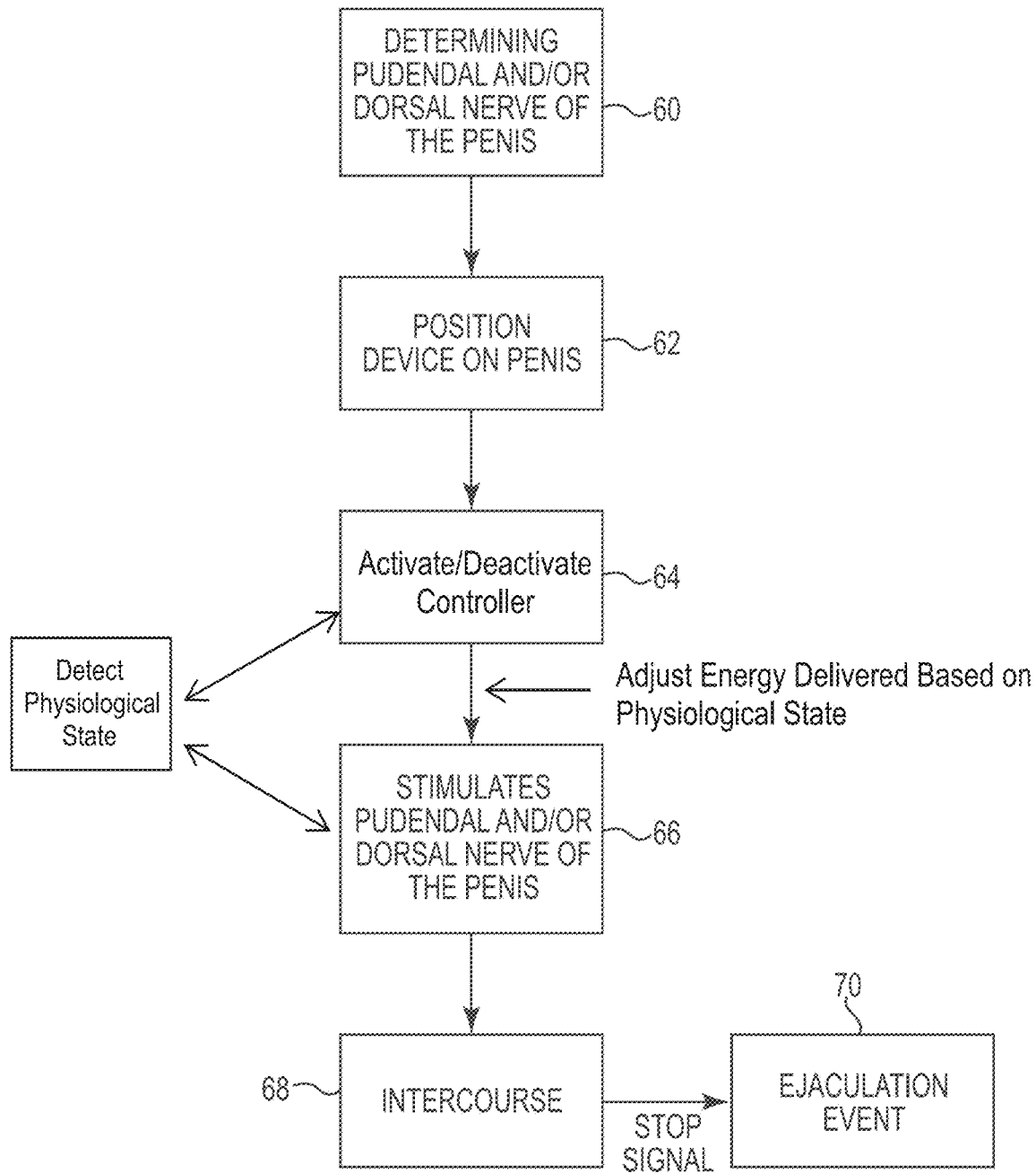
FIG. 15 is a diagram of an exemplary method of treating sexual dysfunction, such as premature ejaculation, according to embodiments of the present invention.
Figure 16:
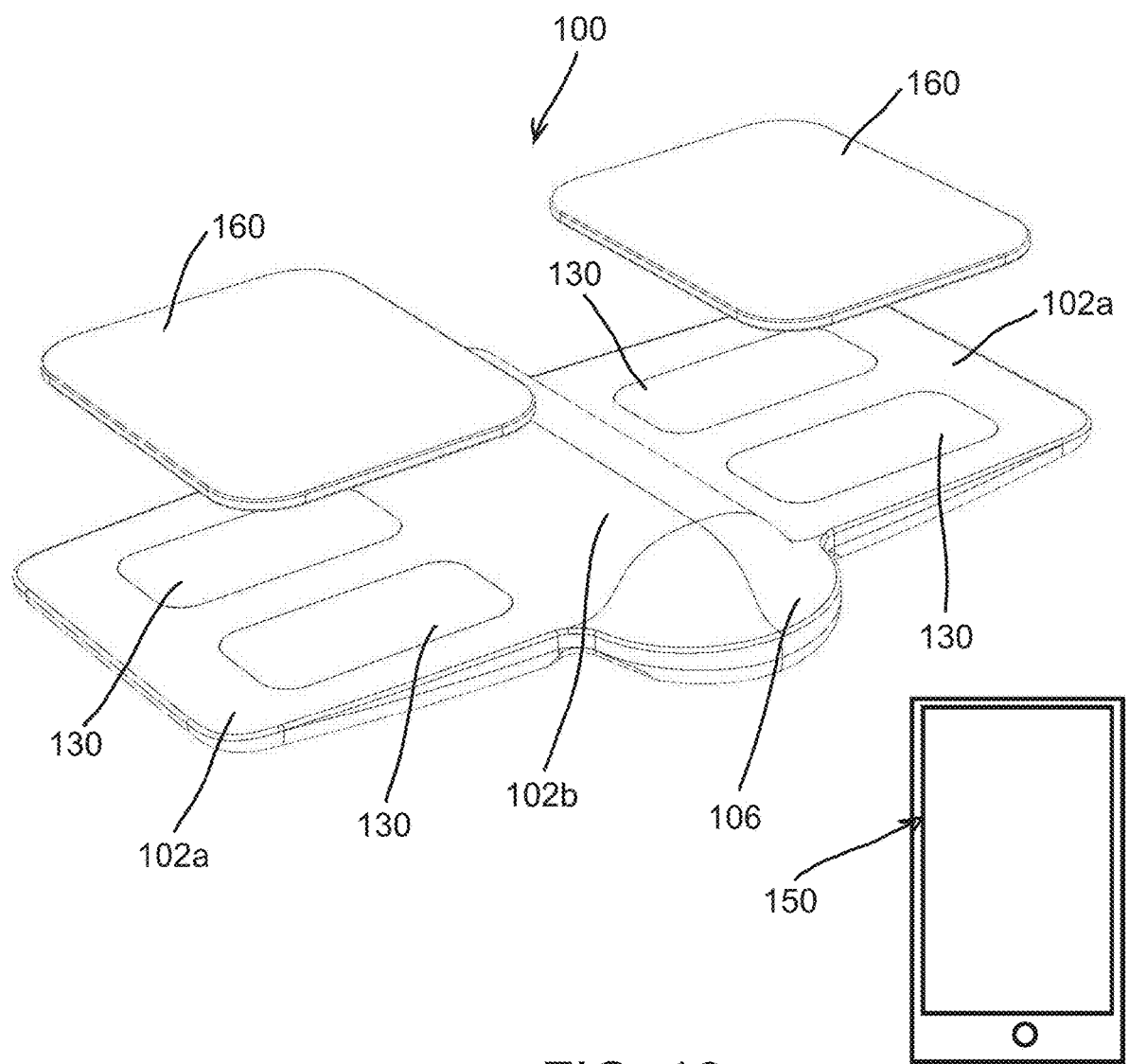
FIG. 16 is a exploded view of a hingeable sexual dysfunction treatment system, with a mobile device controller, according to embodiments of the present invention.
Figure 17:
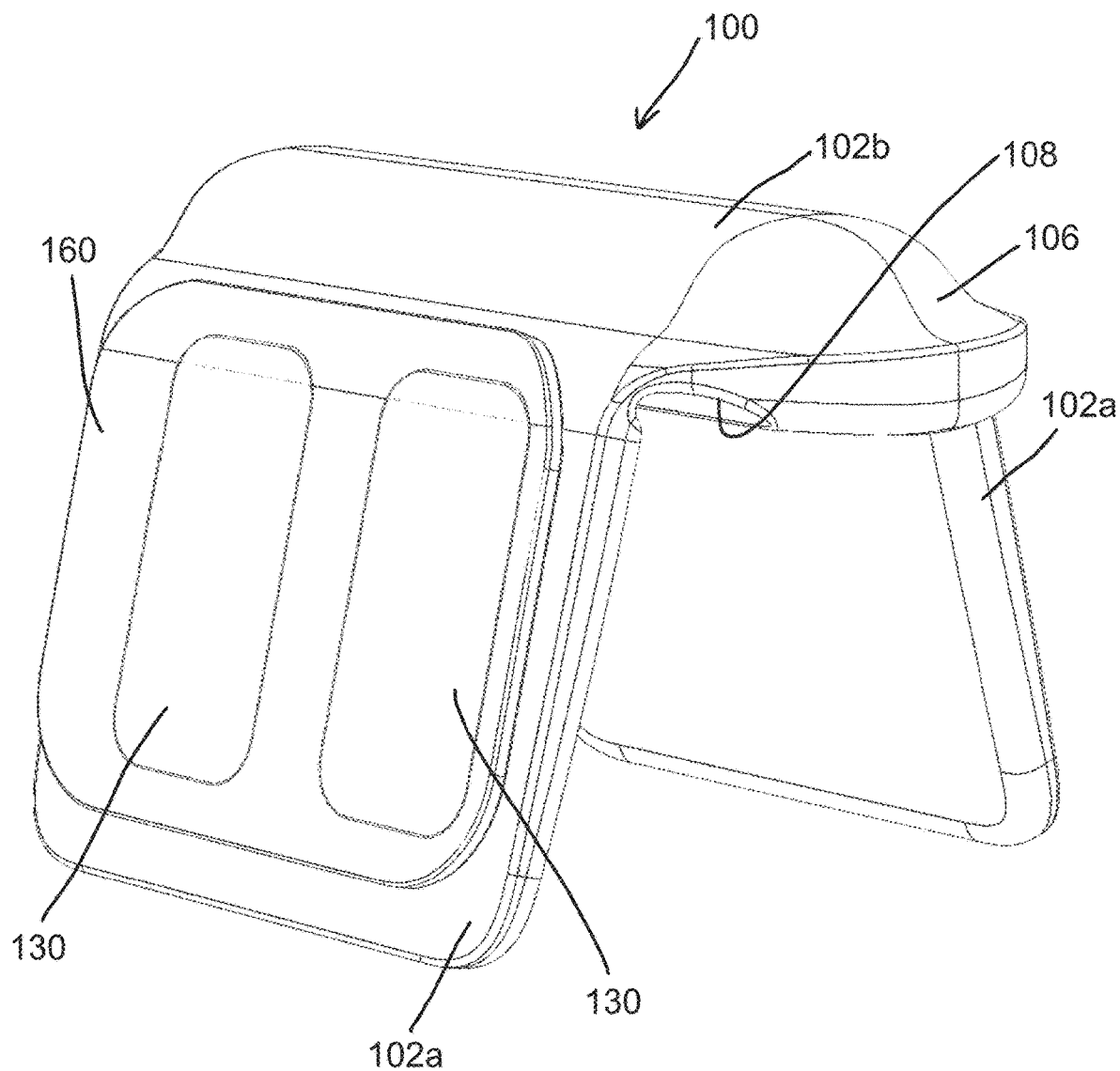
FIG. 17 is a perspective view of a hingeable sexual dysfunction treatment system, pivoted for use about living hinges, according to embodiments of the present invention.
Figure 18:
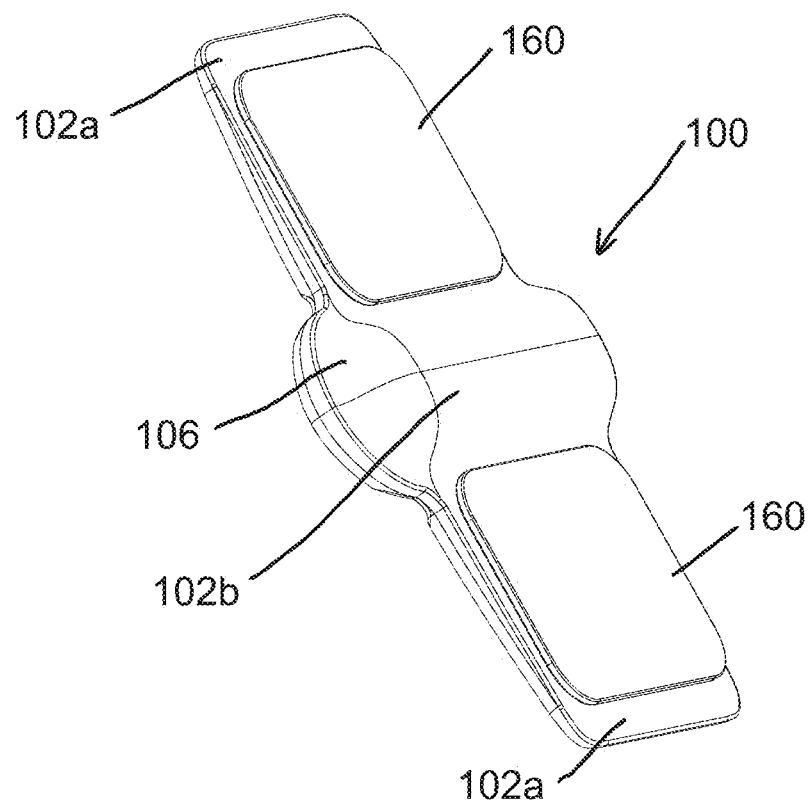
FIG. 18 is a top perspective view of a hingeable sexual dysfunction treatment system, according to embodiments of the present invention.
Figure 19:
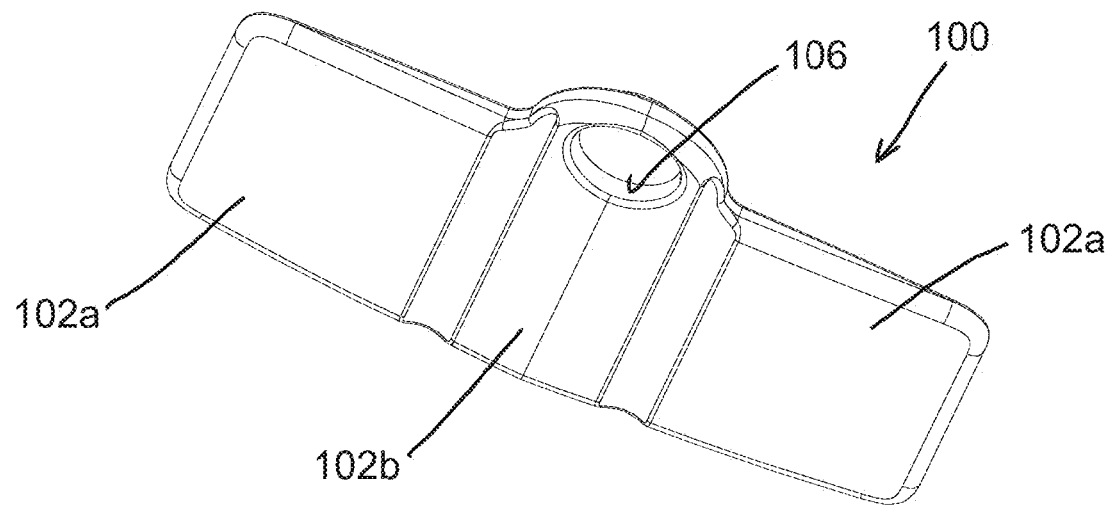
FIG. 19 is a bottom perspective view of a hingeable sexual dysfunction treatment system, according to embodiments of the present invention.
Figure 20:
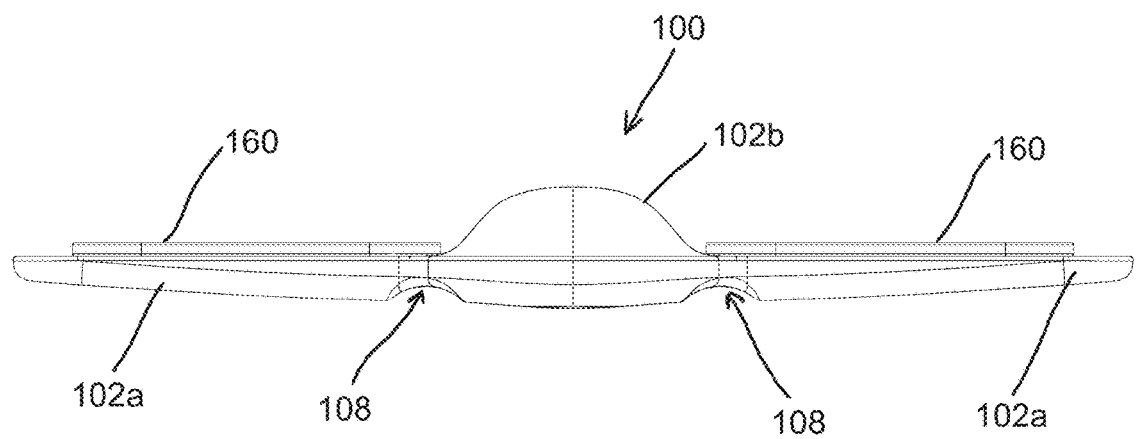
FIG. 20 is a front view of a hingeable sexual dysfunction treatment system, according to embodiments of the present invention.
Figure 21:
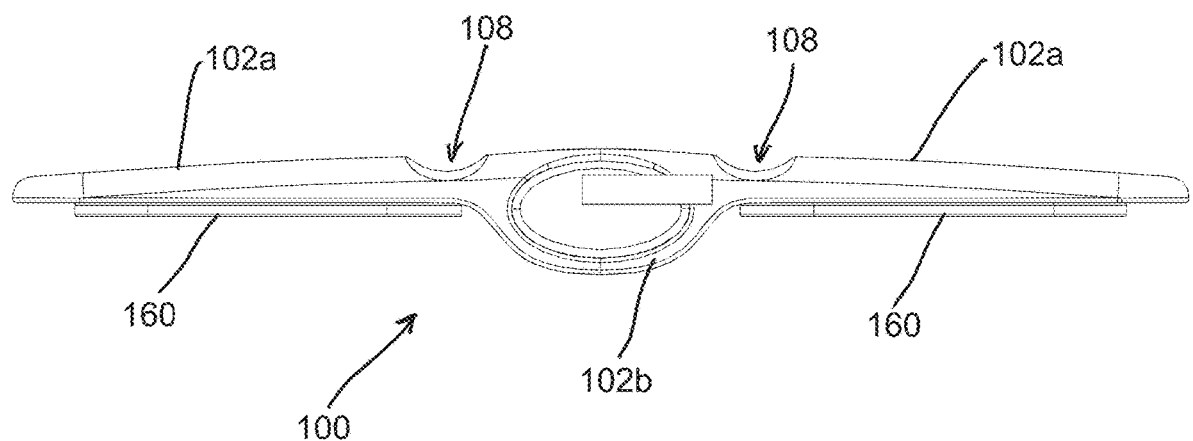
FIG. 21 is a back view of a hingeable sexual dysfunction treatment system, according to embodiments of the present invention.
Figure 22:
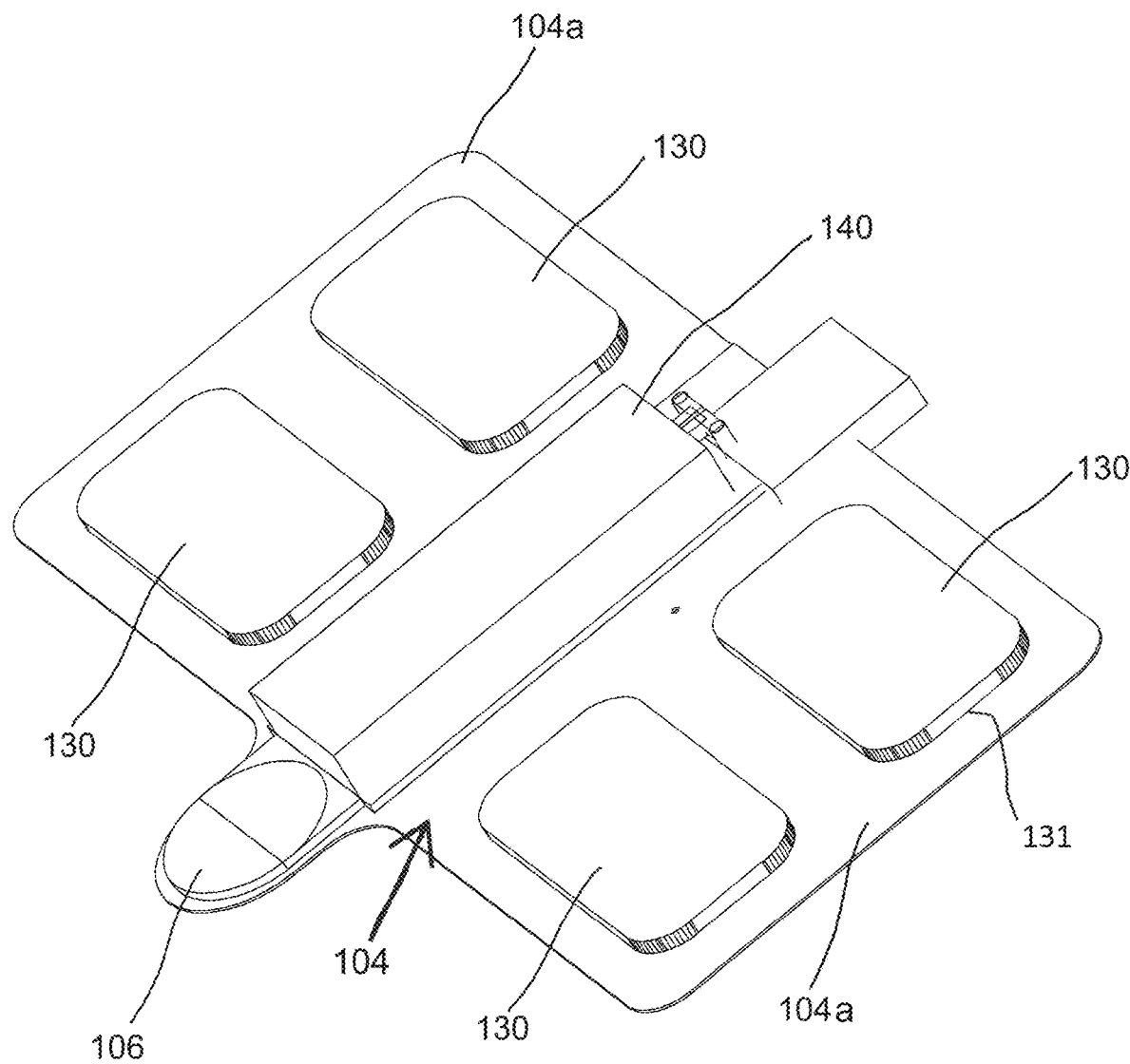
FIG. 22 is a top perspective view of a hingeable sexual dysfunction treatment system, according to embodiments of the present invention.
Figure 23:
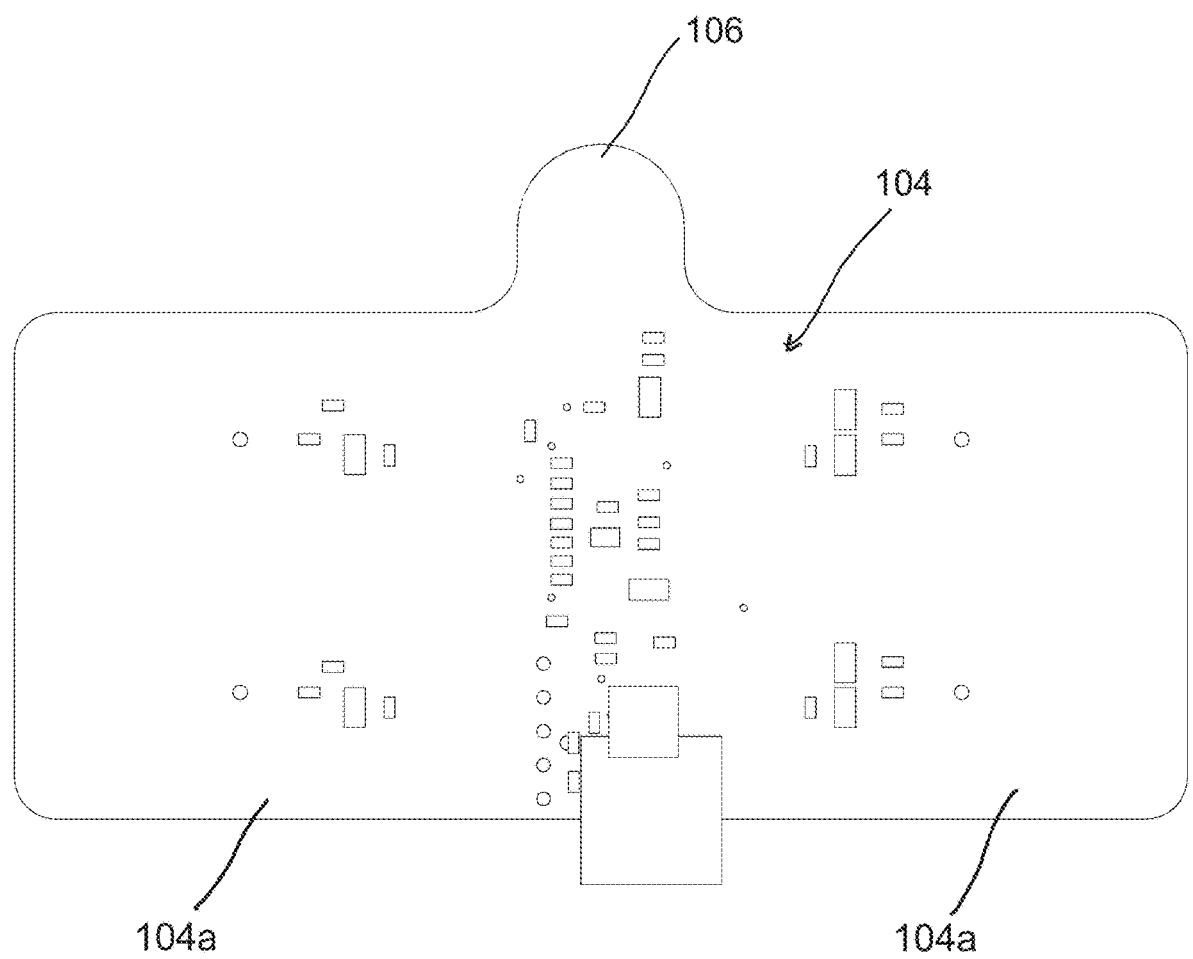
FIG. 23 is a bottom view of a circuit board element for a hingeable sexual dysfunction treatment system, according to embodiments of the present invention.

In use for various embodiments, as detailed in FIG. 15, a user or physician locates the dorsal or pudendal nerve of the penis or pudendal nerves of the penis at step 60. The user or their partner then positions the cuff 20, patch 60, sheath 70, or sleeve 80 on the penis at step 62 such that the one or more transducers 30 are placed proximate the nerve to be treated. In some embodiments, the user or their partner may then remove the film 38A, 38B from the coupling member 36 and position the coupling member 36 between the emitting surface 34 of the transducer 30 and the penis. In step 64, the user or their partner may then use the controller 50 or actuator 84 to activate the one or more transducers 30. The ultrasound generator 30*a* then emits sound waves 34, as shown in step 66. If the device 10 is being used during intercourse, the user and their partner can begin to have intercourse at step 68. Once either the user or partner wants to permit the treated user to ejaculate, the user or the partner may use the controller 50 to switch off the one or more transducers 30 (e.g., ultrasound generator 30*a*), thereby ceasing the sounds wave 34 and permitting the user to ejaculate or orgasm at step 70.

In one embodiment of the invention, the device 10 is capable of increasing or decreasing the intensity of the therapy over a particular period of time. For instance, the device 10 is able to apply an amount of therapy, for example sound energy or electrical energy, which is not perceptible to a patient or user. The device 10 is then able to incrementally increase the intensity of the therapy to a pre-set level. After a certain period of time or a predetermined amount of time, the device 10 is able to incrementally decrease the intensity of the therapy. The therapy is capable of cycling the therapy levels for a selectable or automatic period of time. In another example embodiment of the invention, a user or third party is able to manually adjust the intensity level and/or duration of the therapy session.

In still another embodiment of the invention, the device 10 may be implantable into a patient. The implantable device or system 10 includes a biocompatible housing, internal therapy circuitry such as an ultrasound producing or electrical producing system. Leads may be implanted and disposed proximate a nerve, such as the dorsal nerve or pudendal nerve of the penis, that is capable of treating premature ejaculation.

The implantable system may be implanted in an office setting by using a delivery system that includes a delivery needle that may be inserted into the pubis region of a patient. In one example embodiment, the delivery needle may be inserted into a patient's urethra to deliver the system 10 into the patient's pubis. In yet another example embodiment, the delivery needle may be inserted transabdominally to deliver the system into the pubis region of the patient. The device 10 may be positioned in an anterior portion of the pubis or the base of the penis such that it is positioned proximate the dorsal nerve or pudendal nerve. Ideally, the device 10 is positioned proximate the dorsal nerve of the penis or pudendal nerve and may be activated transdermally by the controller 50. In the implantable embodiment, the ultrasound generator 30a or electrical generator 30b includes a rechargeable power supply that can be recharged transdermally (e.g., wirelessly). One of the advantages of the implantable embodiment is that a user's partner is unaware of the use of the system 10.

In another embodiment of the invention, as illustrated in FIGS. 16-27, a foldable, flexible, or hingeable device 100 can include a housing or support 102, a controller 150 circuit board element 104, one or more electrodes or pairs of electrodes 130, and a power supply 140 (e.g., battery). The housing or support 102 can include foldable wings or electrode containment portions 102a and a central body portion 102b. The device 100 is hingeable at living hinges or portions 108 such that the device 100 can be selectively manipulated and placed with the electrodes 130 contacting targeted tissue or nerves for stimulation. Further, a button, touch sensor, or other actuation mechanism 106 can be included to control the device 100. The actuation mechanism 106 can be pressed or touched to turn the device 100 on and off, pressed, touched, or tapped to increase or vary stimulation, and the like. The power supply 140 and other components and circuitry can be housed within or supported by the central body portion 102b.

The circuit board element 104 is contained within or supported by the housing 102, with foldable circuit portions 104a secured within the foldable wing portions 102a such that the electrodes 130 extend out from the wing portions 102a (e.g., via openings or apertures in the housing 102) for positioning and contact with patient tissue. The foldable portions 104a fold or pivot at circuit hinge portions 104b (e.g., FIG. 26).

The housing or support 102 can comprise of one or more layers of a flexible material such as a woven fabric, a plastic strip (such as PVC, polyethylene or polyurethane), or a latex strip. The internal components of the device 100 such as the circuit board element 104 and the electrodes 130 can be sandwiched between one or more layers. The housing 102 can comprise one or more openings 131 proximate the electrodes 130 to allow or permit the electrodes to contact a user's skin. The housing 102 can also comprise conductive portions positioned over the electrodes 130 to allow for the electrodes to be protected but allow for the stimulation treatment to pass through the conductive material and onto the user's skin. The housing 102 can comprise any material that is disposable or can be cleaned or sterilized.

In another embodiment of the present invention, the housing 102 can comprise a molded flexible material manufactured from a PVC, polyethylene or a polyurethane material. The housing 102 can have an interior configured to hold the circuit board element 104 and the electrodes 130. The molded housing 102 can also include openings or recesses 131 for holding the electrodes 130, sensors, switches, and other features that are in operative communication with the device 100.

In one example embodiment of the present invention, the electrode containment or wing portions 102a can have a thickness generally less than, greater than, or equal to a thickness of the central body portion 102b. The variation in the thickness of the electrode containment or wing portion portions 102a can aid in enabling their flexing with respect to the central body portion 102b. The housing 102 can also comprise one or more web portions 108 extending between and connecting the electrode containment or wing portions 102a and the central body portion 102b. The web portion 108 can have a thickness generally less than a thickness of the electrode containment portions 102a and the central body portion 102b to facilitate easier flexing of the electrode containment portions 102a.

In operation, the device 100 provides non-uniform and changing effective electrical stimulation timing of pulses with varying effective frequencies to "confuse" nerves and receptors involved in the ejaculatory process. The targeted neural network runs between the base of the penis and the spinal cord, within the region of the perineum. This is the anatomical area closest to those nerves and receptors involved in the ejaculatory process. There are other excitable tissues in the region that may receive electrical stimuli as well via the device 100. The device 100 is placed transperineally, with the electrodes 130 crossing the plane of nerves running parallel with the urethra.

The electrical stimulation of the device 100 is directed through the electrodes 130 using a non-uniform selection from one electrode to another. This stimulation pattern results in varying length pathways and a variance of time and physical distance for stimulations contacting those nerves and receptors. This results in an "ultra" neural stimulation at various times and directions within the ejaculatory neural network, thereby providing a varying of absolute and relative refractory time periods as well as their baseline resting membrane potential. Stimulations occur over varying parts of the refractory periods of the excitable cells in the perineal region, thereby resulting in neuromodulation of the ejaculatory process via neuro-confusion. This "ultra confusion" is imparted on the nerves and receptors, which promotes a modulation of nerve signal conduction, which results in time prolongation of ejaculation. Because the stimuli are constantly varying, there is a dramatic reduction or elimination of neurologic adaption to electrical signals, as well as a more effective neural modulation of the pathway.

The device 100 can be controlled and adjusted with a remote or mobile device 150, such as a smartphone and executed mobile app, in operative wireless communication with the circuit board element 104. The mobile app can receive feedback, monitor operation, log device and treatment information and data, analyze device and treatment information and data, and the like. The mobile device 150 can be used and operated by the patient, the patient's partner, and other authorized third parties.

As illustrated in FIGS. 16-21, conductive electrode gel pads 160 can be provided for placement and adherence over the one or more of the electrodes 130 during use. A single gel pad 160 can cover a single electrode 130, or two adjacent electrodes 130. The gel pads 160 can be replaced between uses of the device 100, which provides an economic savings to the user and prevents additional waste from entering the landfills. The housing 102 of the device 100 can include a raised ridge portion that extends about the electrode containment or wing portions 102a and 102b. The raised ridge portion aids a user in positioning the gel pads 160 over the electrodes 130. While the device 100 of the invention is described as being reusable, it is also contemplated herein that the device 100 can be manufactured to be a single-use disposable item.

Figure 24:
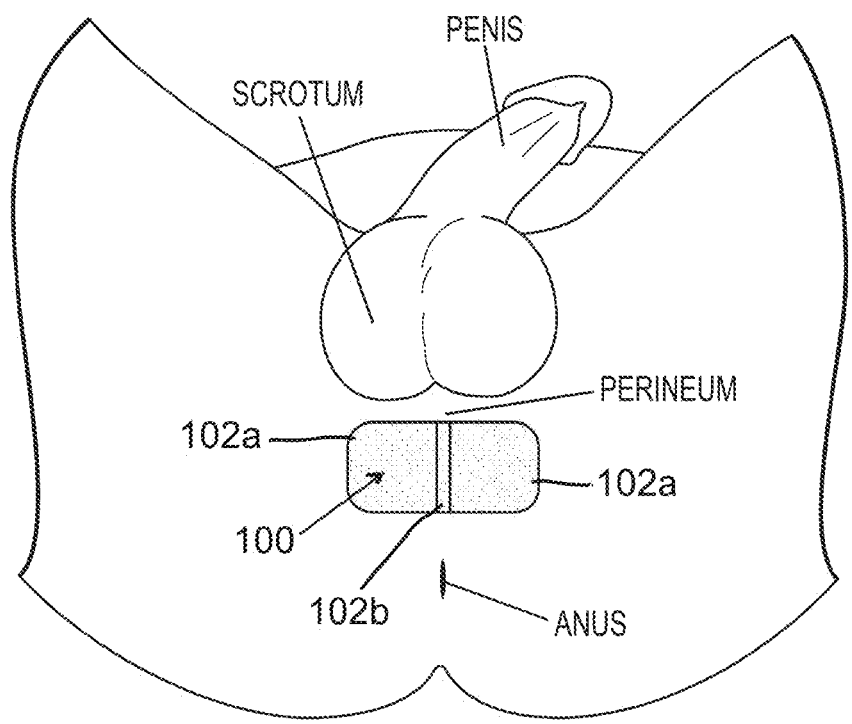
FIG. 24 is a view of an example anatomical placement of a hingeable sexual dysfunction treatment system, according to embodiments of the present invention.
Figure 25:
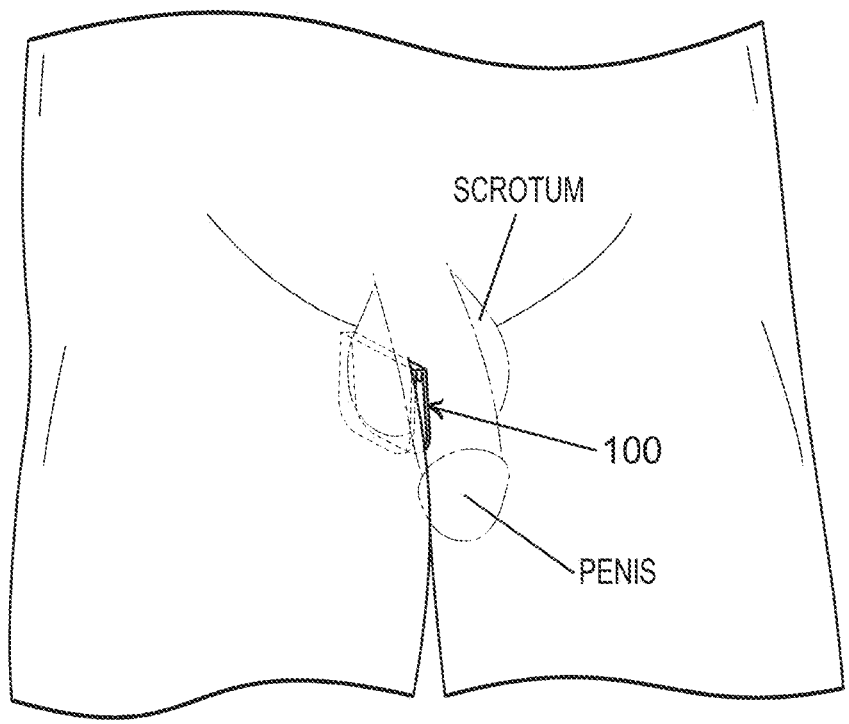
FIG. 25 is a view of hinged or pivotal therapeutic placement of a hingeable sexual dysfunction treatment system, according to embodiments of the present invention.

FIGS. 24-25 show an example placement of the device 100 in use. In this example, the device 100 is placed on a male patient to facilitate effective treatment and therapy. FIG. 24 demonstrates the initial application of the device 100 in a generally non-hinged configuration at the perineum. FIG. 25 depicts the device 100 after hingeable placement at the perineum. It can be seen that the device 100 is folded and located against the user's thighs and buttocks. Exact placement will vary depending upon user's anatomy and optimized treatment location.

Figure 26:
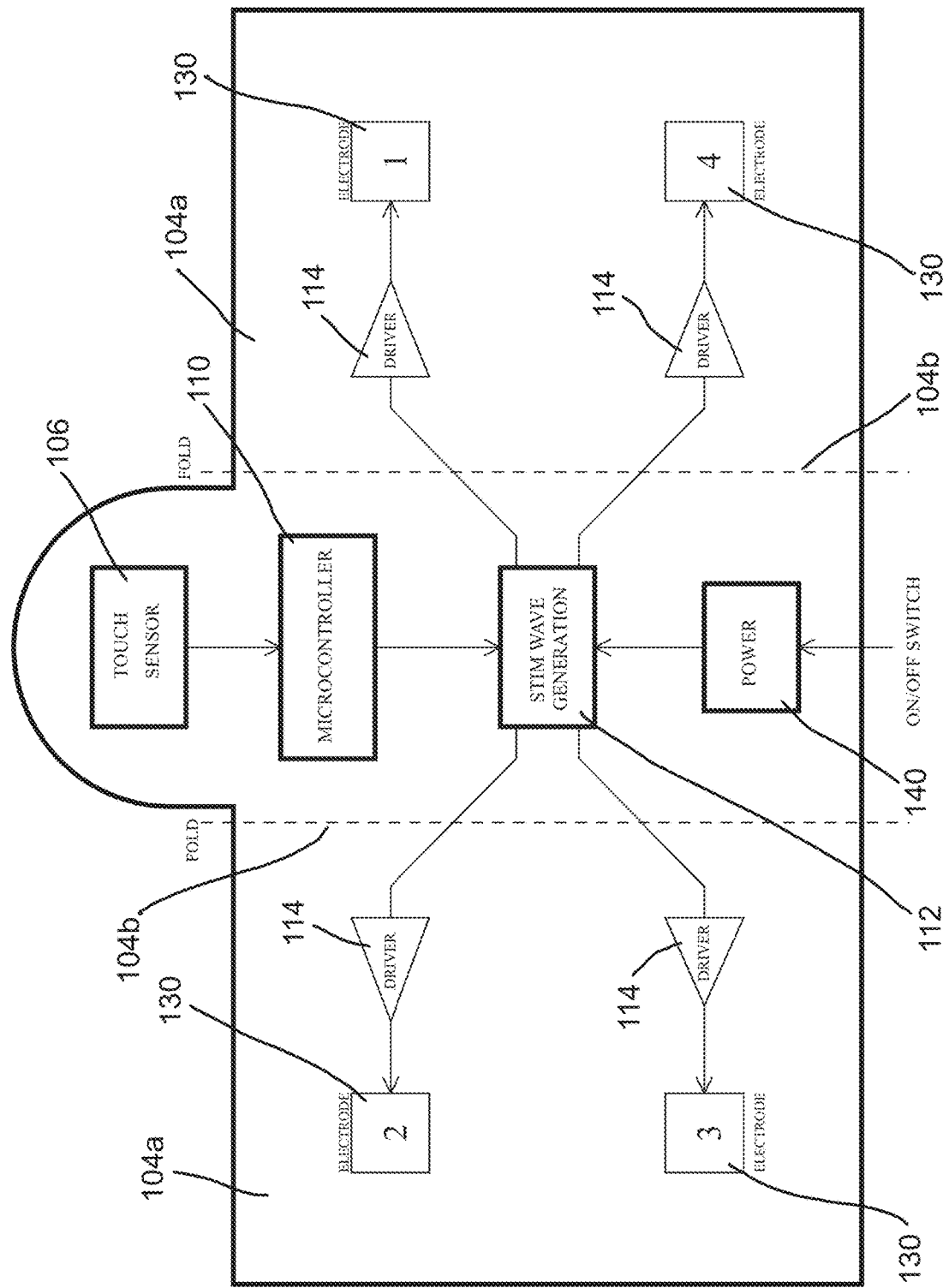
FIGS. 26-27 are schematic block diagrams of a circuit board elements and operative components and features for a hingeable sexual dysfunction treatment system, according to embodiments of the present invention.
Figure 27:
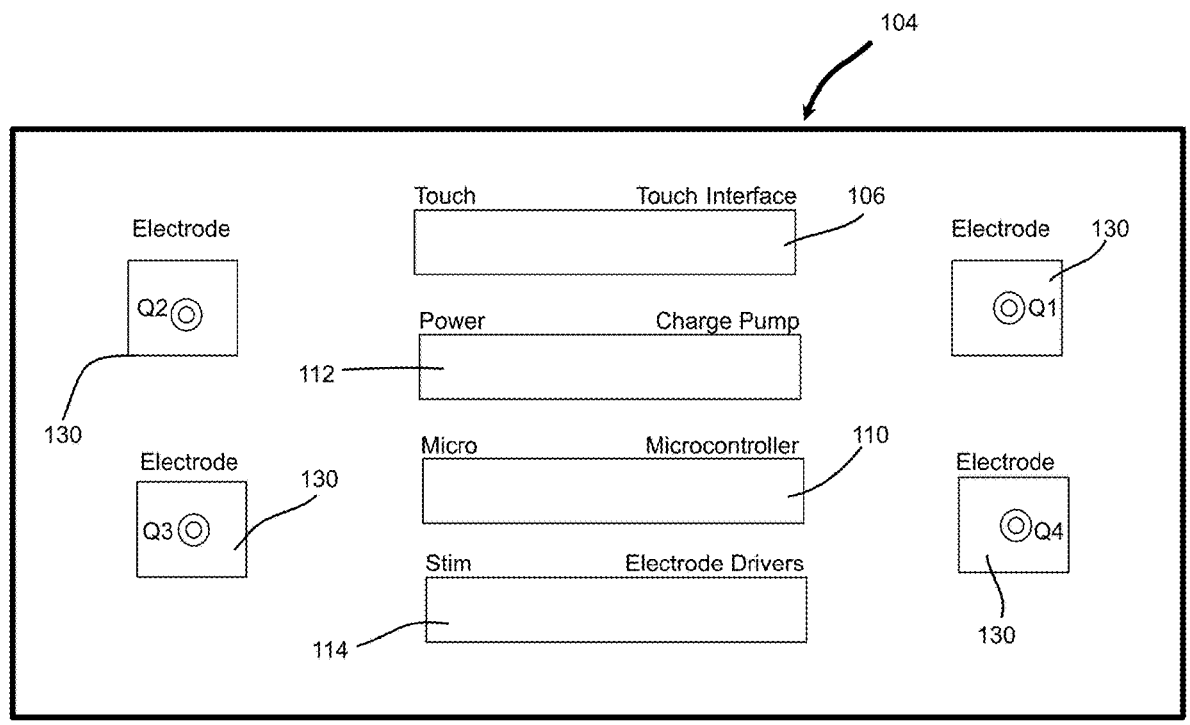

As shown in the schematic diagrams of FIGS. 26-27, embodiments of the device 100 include a touch sensor 106, a microcontroller 110, a stim wave generator 112, a power source 140, a plurality of stim drivers 114, and the plurality of electrodes 130. The power source 140 of the device 100 used to control the components of the device 100 can be rechargeable. As such, the device 100 can include a charging port or wireless charging technology. In another example embodiment of the present invention, the power source 140 can be charged by wireless transmission through the one or more electrodes 130. In this way, the one or more electrodes 130 are able to provide a dual function of providing treatment and charging the power source 140. The device 100 can include a wireless charger that is able to interface with a portion of the device, or one or more of its electrodes 130 to charge the power source 140.

The onboard power source 140 allows the device 100 to generate four or more stim vectors through the electrodes 130 that vary in voltage and frequency. For example, the vector sequence can include the following pattern: electrode 1 to electrode 2; electrode 1 to electrode 3; electrode 4 to electrode 3, and electrode 4 to electrode 2. This pattern can be repeated or alternate between different patterns. A user selected voltage target changes the pulse frequency as well. Other effective therapeutic vector patterns and control adjustments can also be utilized without deviating from the spirit and scope of the present invention. For instance, the vector drives can be random or nearly random, the voltage, frequency and other vector patterns can be changed, a sequence or modulate voltage and/or frequency can be adjusted to obtain the highest level of neural confusion, voltage and frequency and applied modulations can be independently controlled, and stimulation and un-stimulation (or varied with a pattern) can occur that results in triggering the final ejaculation event via user control.

The device 100 is able to vary any of its parameters to aid in the "ultra confusion" of targeted nerves and pathways. The following are some examples of device parameters that can be varied:

Voltage and/or current levels
Voltage and/or current duration
Stim delivery frequency or period
Energy delivered
Impedance
Applied stim vector pattern and sequencing
Modulation of one or more of the above variables The present invention can also include one or more sensors that are able to sense an approaching ejaculatory event and then alter or modulate one of the above device parameters in order to provide effective stimulation therapy to delay the ejaculation. In one example embodiment, the electrodes 130 are also capable of acting as a sensor. In this embodiment, the electrodes 130 are able to sense a change in the skin potential that signals an approaching ejaculatory event. Other sensors may also be employed. For instance, stretch sensors can be used to detect the peristaltic waves or contractions of the penis. These contractions typically precede and coincide with an ejaculation. When a peristaltic contraction is detected the device 100 can modulate the therapy, thereby confusing the nerves until the peristaltic contractions stop. This process can be repeated until the user or their partner desires the ejaculatory event to occur, at which point they can turn off or reduce the therapy being delivered.

Sensors for detecting physiological and device parameters can include accelerometers, stretch sensors, impedance sensor—(may change nearing the event or in relation to other factors), temperature sensor, motion sensors (1, 2 and 3D accelerometers for force, distance, rep rate, etc.), photosensors with or without LED light source (e.g., to sense heart rate, blood flow rate), and/or pressure sensors (e.g., measure blood pressure or changes in penis diameter). Other sensors and detection devices are also considered to be within the spirit and scope of the invention.

Figure 37:
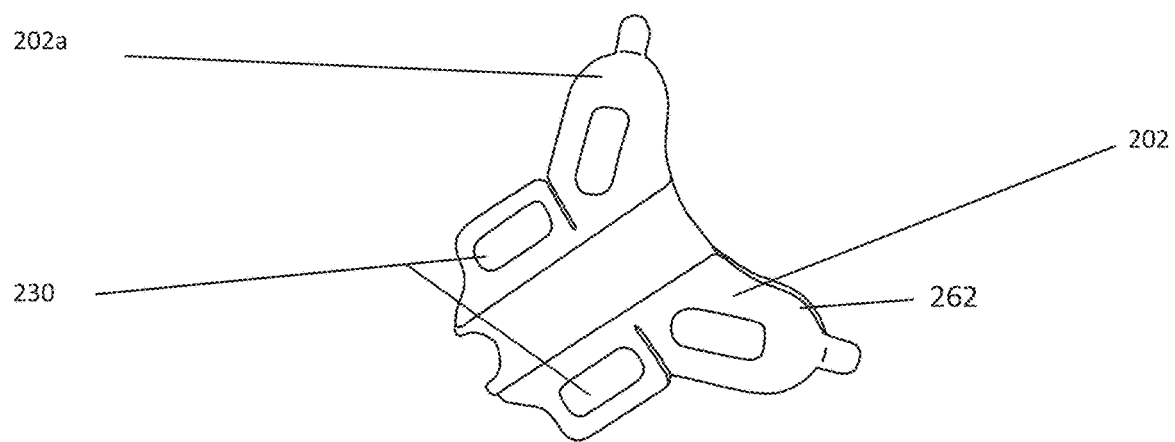
FIG. 37 is a top view of a hingeable sexual dysfunction treatment system, according to embodiments of the present invention.

In yet another embodiment of the invention, as illustrated in FIGS. 28-47, a foldable, flexible, or hingeable device 200 can include a housing or support 202, a controller or circuit board element 204 (see FIG. 39), one or more electrodes or pairs of electrodes 230 (see FIG. 37), and a power supply 240 (e.g., battery). Similar to other embodiments, the housing 202 can include foldable wings or electrode containment portions 202a and a central body portion 202b. The device 200 is hingeable at living hinge or web portions 208 such that the device 200 can be selectively manipulated and placed with the electrodes 230 contacting tissue locations for stimulation and a predetermined therapy outcome. Further, a button, touch sensor, or other actuation mechanism 206 can be included. The actuation mechanism 206 can be pressed or lightly touched to turn the device 200 on and off, pressed or tapped to increase or vary stimulation, and the like. The power supply 240 and other components and circuitry can be housed within the central body portion 202b or can be detached for charging or replacement.

Figure 40:
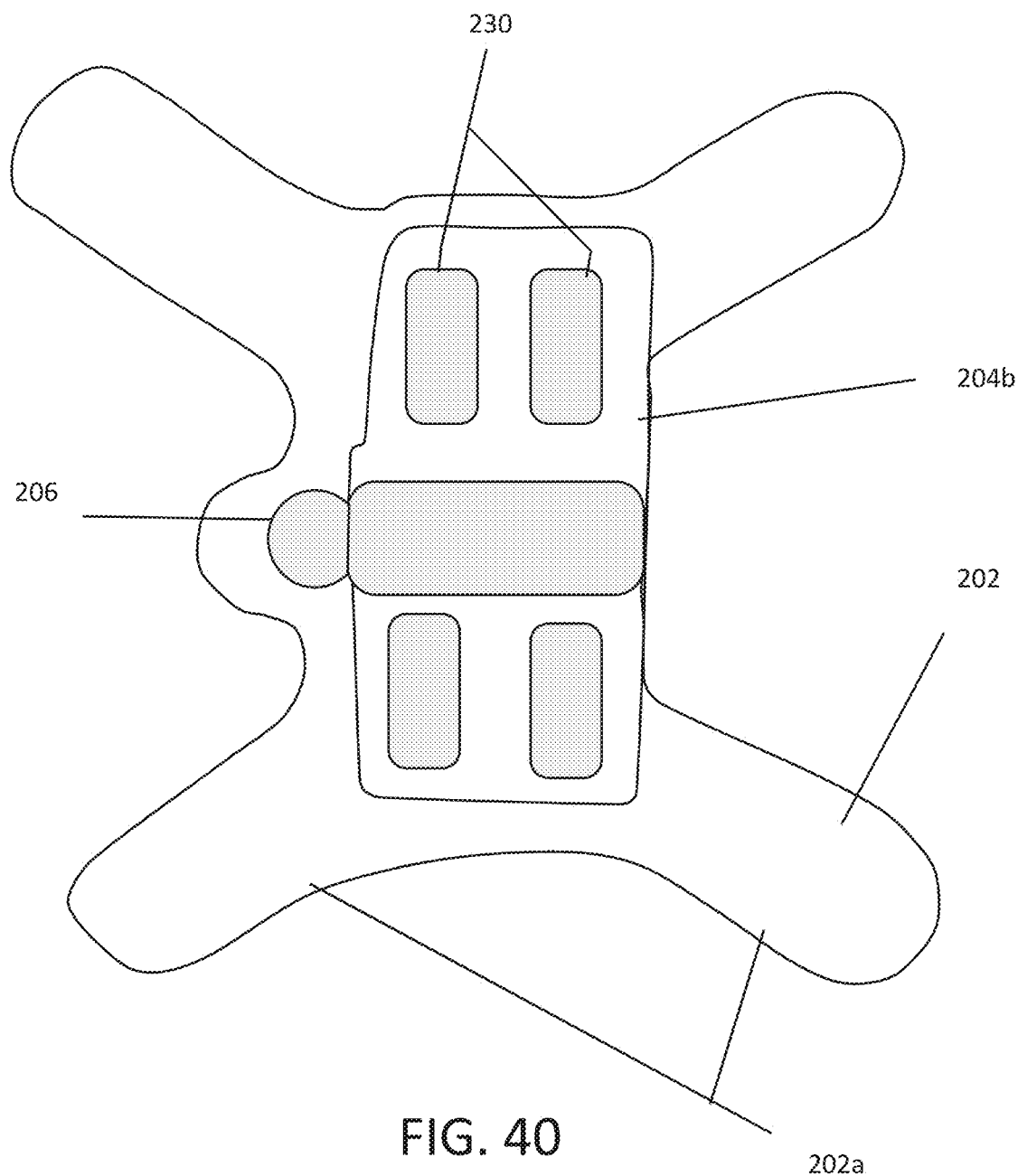
FIG. 40 is a top view of a hingeable sexual dysfunction treatment system with individual wing portion, according to embodiments of the present invention.
Figure 41:
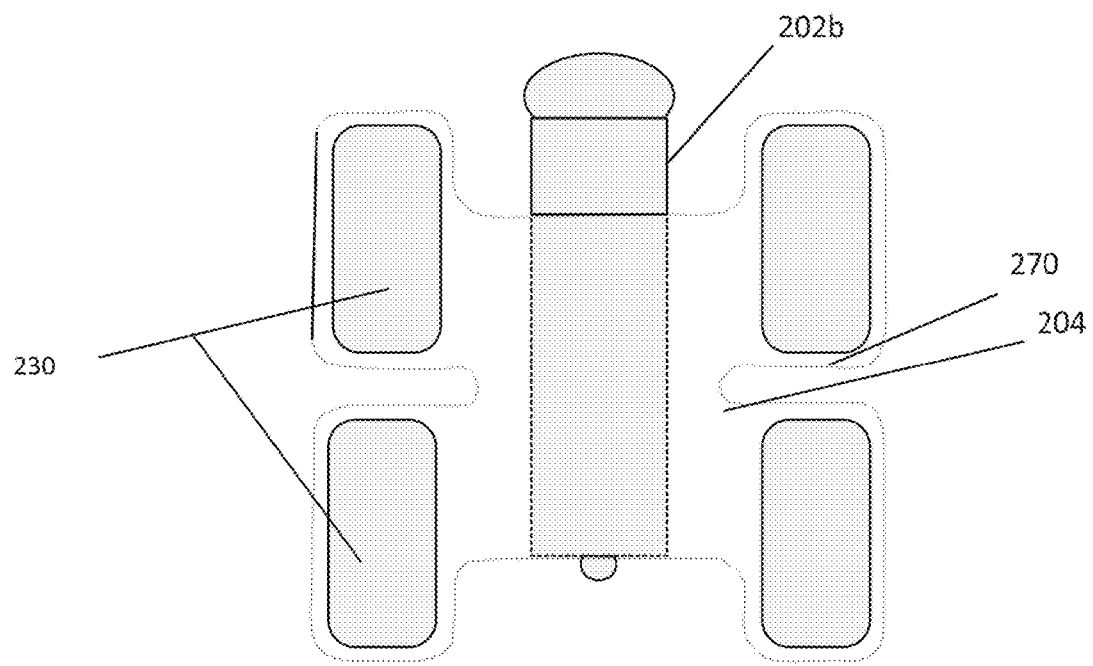
FIG. 41 top view of a hingeable sexual dysfunction treatment system with individual wing portions, according to embodiments of the present invention.
Figure 42:
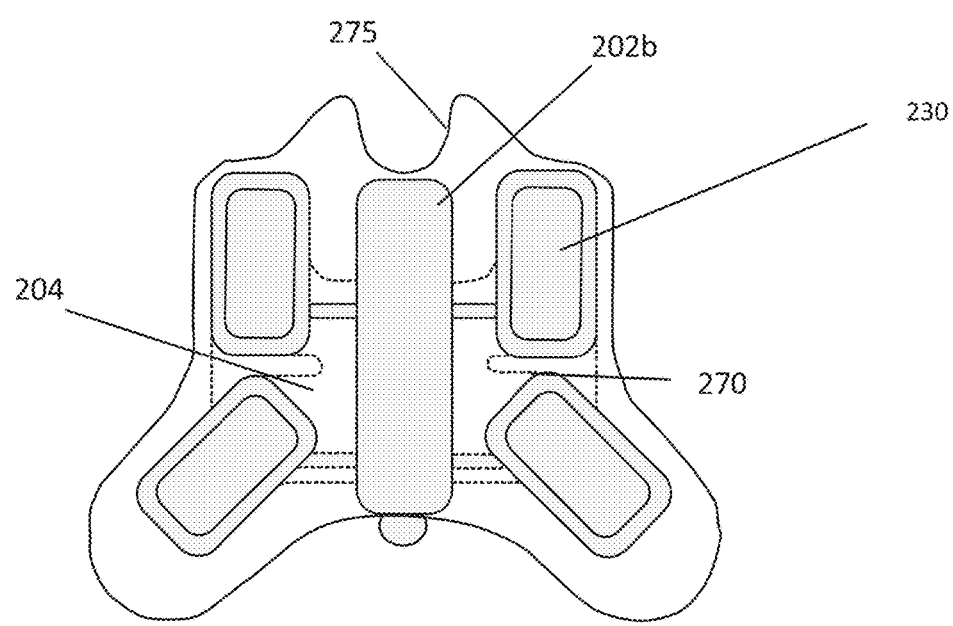
FIG. 42 top view of a hingeable sexual dysfunction treatment system with cutout and slits, according to embodiments of the present invention.
Figure 43:
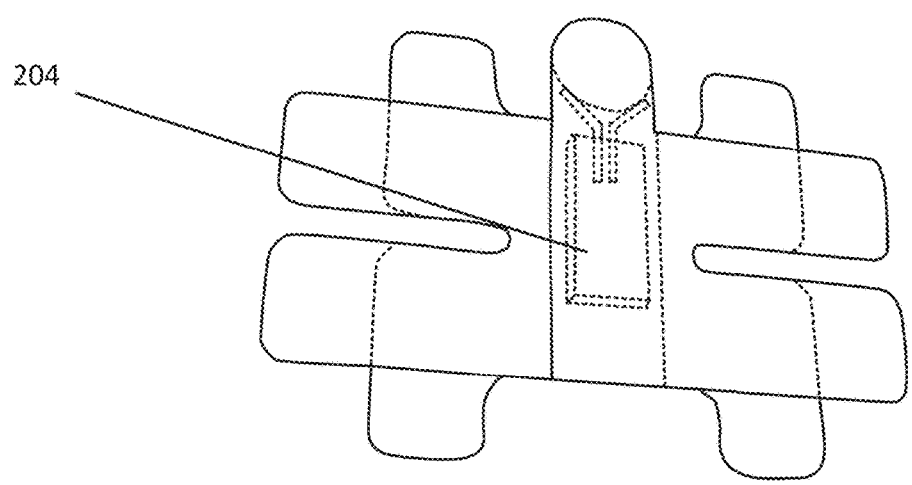
FIG. 43 is a perspective view of a hingeable sexual dysfunction treatment system with an attachable power supply and control module, according to embodiments of the present invention.
Figure 44A:
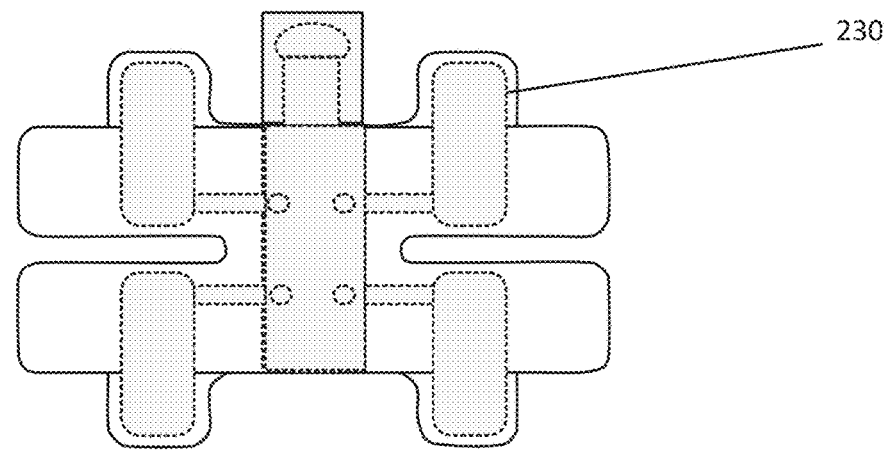
FIG. 44A is a top view of the hingeable sexual dysfunction treatment systems of FIG. 43, according to embodiments of the present invention.
Figure 44B:
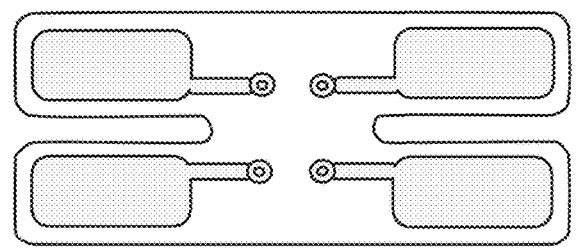
FIG. 44B are top view of an electrode layout for a hingeable sexual dysfunction treatment system, according to embodiments of the present invention.

As particularly illustrated in FIG. 40-42, the circuit board element 204 is contained within or supported by the housing 202, with foldable circuit portions 204 a secured within the foldable wing portions 202a such that the electrodes 230 extend out from the wing portions 202 a (e.g., via openings or apertures in the housing 202) for positioning and contact with patient tissue. The foldable portions 204 a fold or pivot at circuit hinge portions similar to those of the other embodiments described herein.

As discussed with other embodiments, the housing 202 can comprise of one or more layers of a flexible material such as a woven fabric, a plastic strip (such as PVC, polyethylene or polyurethane), or a latex strip. The internal components of the device 200 such as the circuit board element 204 and the electrodes 230 can be sandwiched between one or more layers. The housing 202 can comprise one or more openings proximate the electrodes 230 to allow or permit the electrodes to contact a user's skin. The housing 202 can also comprise conductive portions positioned over the electrodes 230 to allow for the electrodes to be protected but allow for the stimulation treatment to pass through the conductive material and onto the user's skin. The housing 202 can comprise any material that is disposable or can be cleaned or sterilized.

Figure 46:
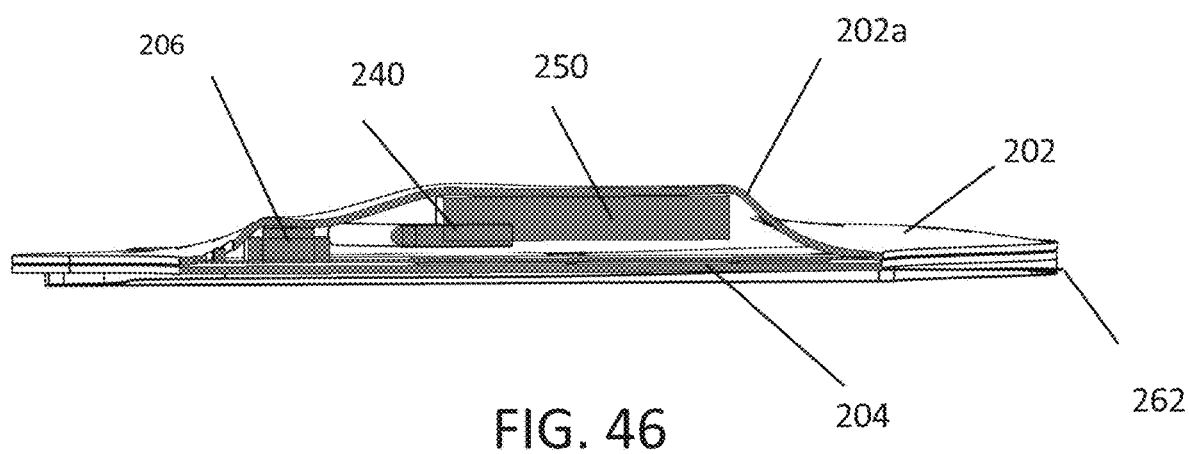
FIG. 46 is a cross sectional view of a hingeable sexual dysfunction treatment system, according to embodiments of the present invention.
Figure 47:
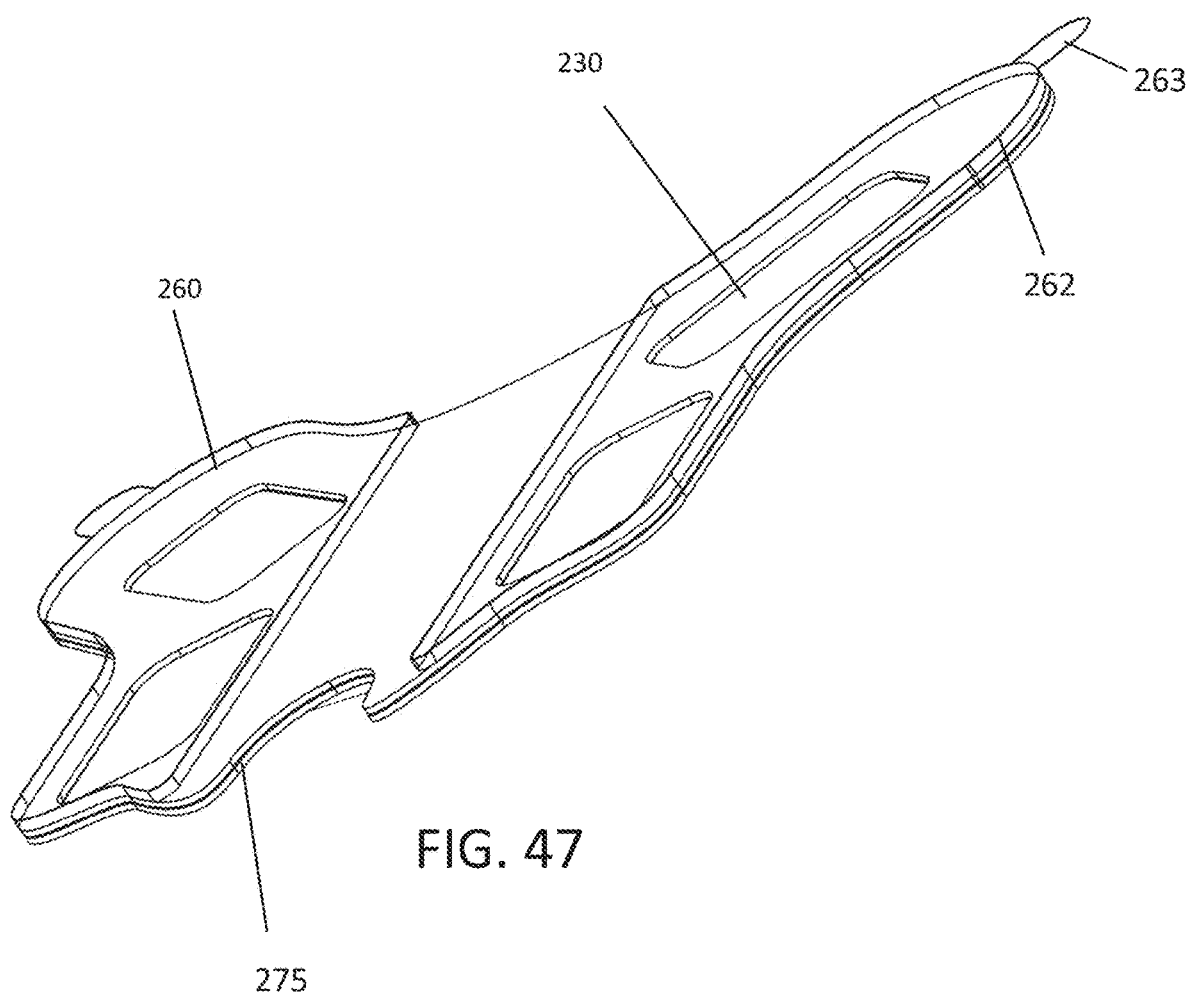
FIG. 47 is a perspective top view of hingeable sexual dysfunction treatment systems, including replaceable gel pads, according to embodiments of the present invention.
Figure 48:
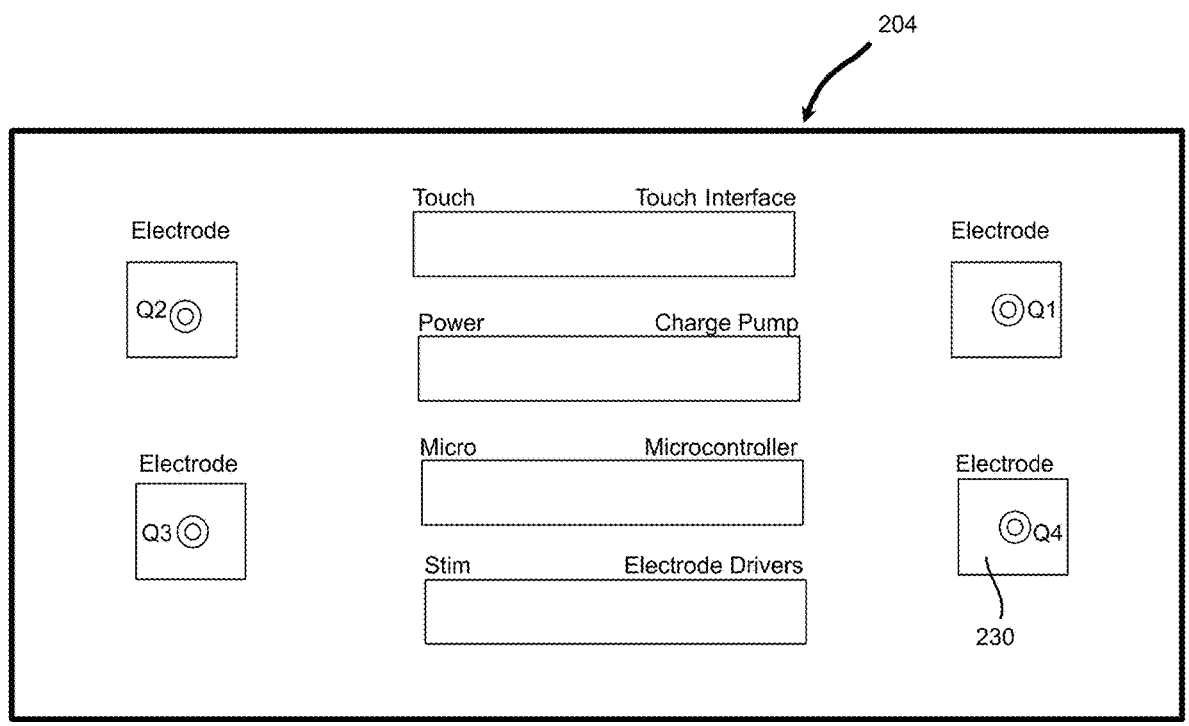
FIGS. 48-51 are electronic schematics of a sexual dysfunction treatment system according to example embodiments of the invention.
Figure 49:
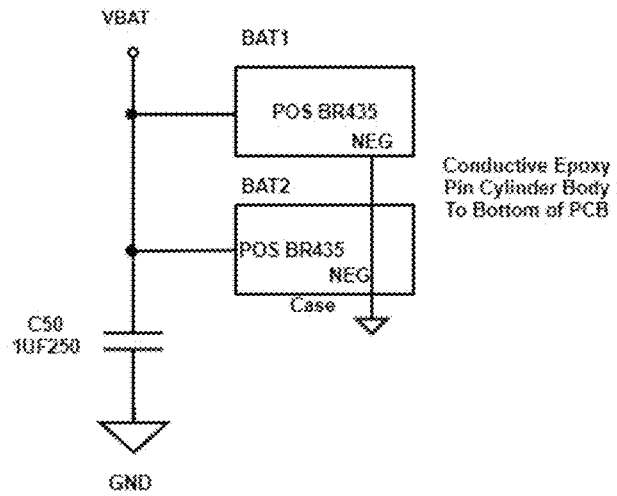
Figure 49:
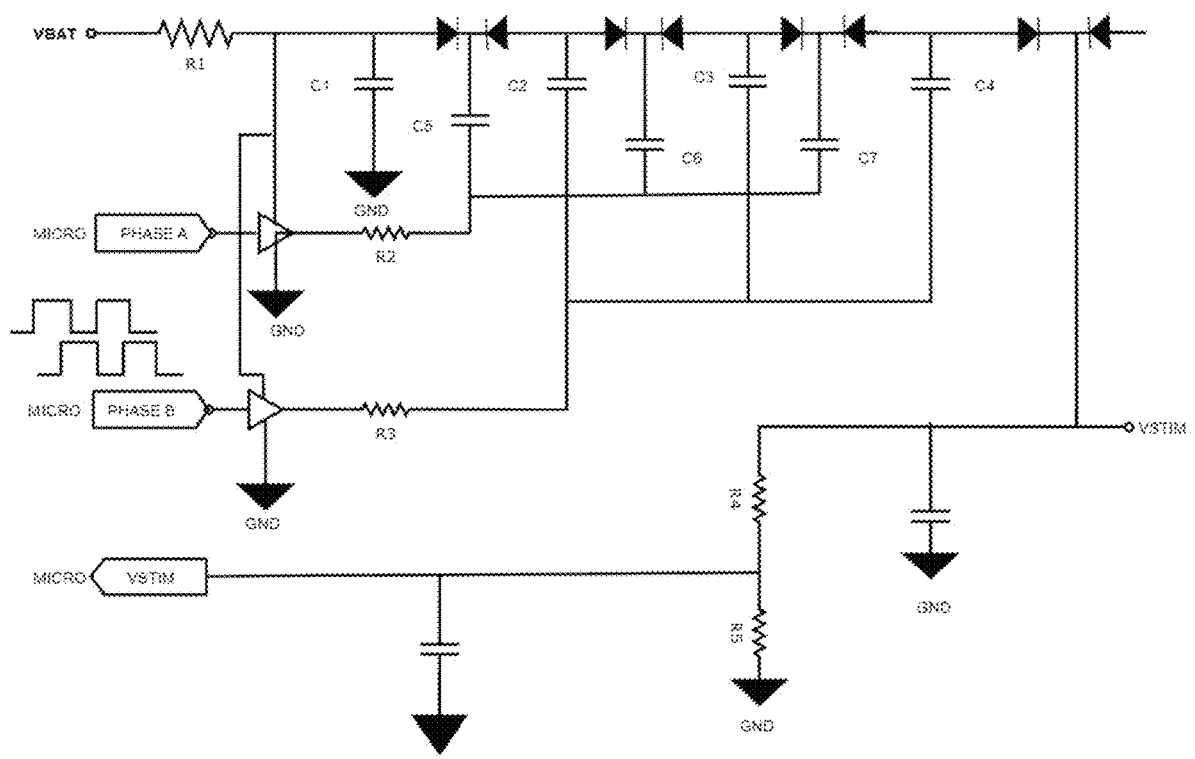
Figure 50:
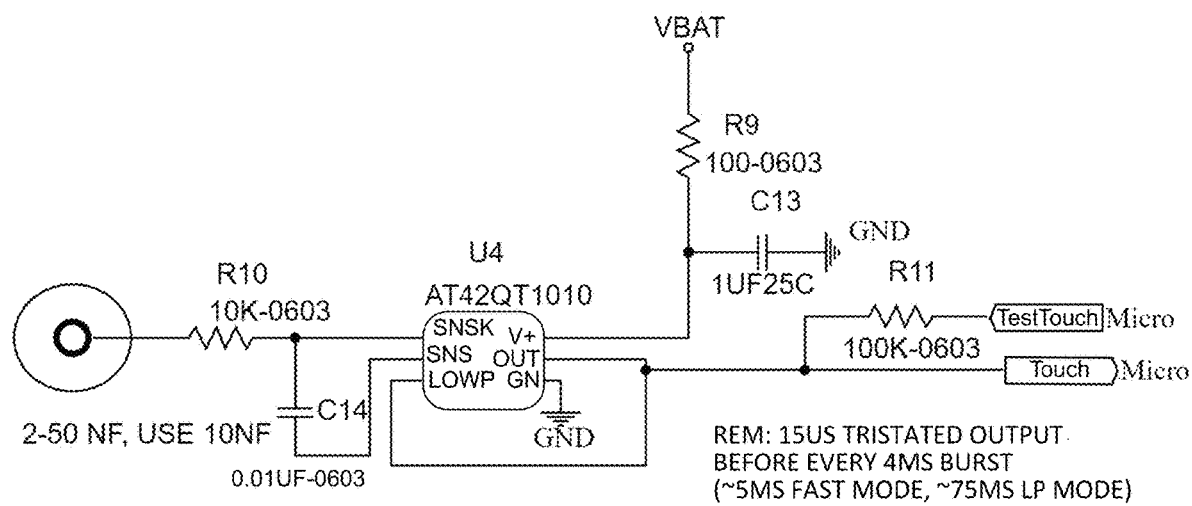
Figure 51:
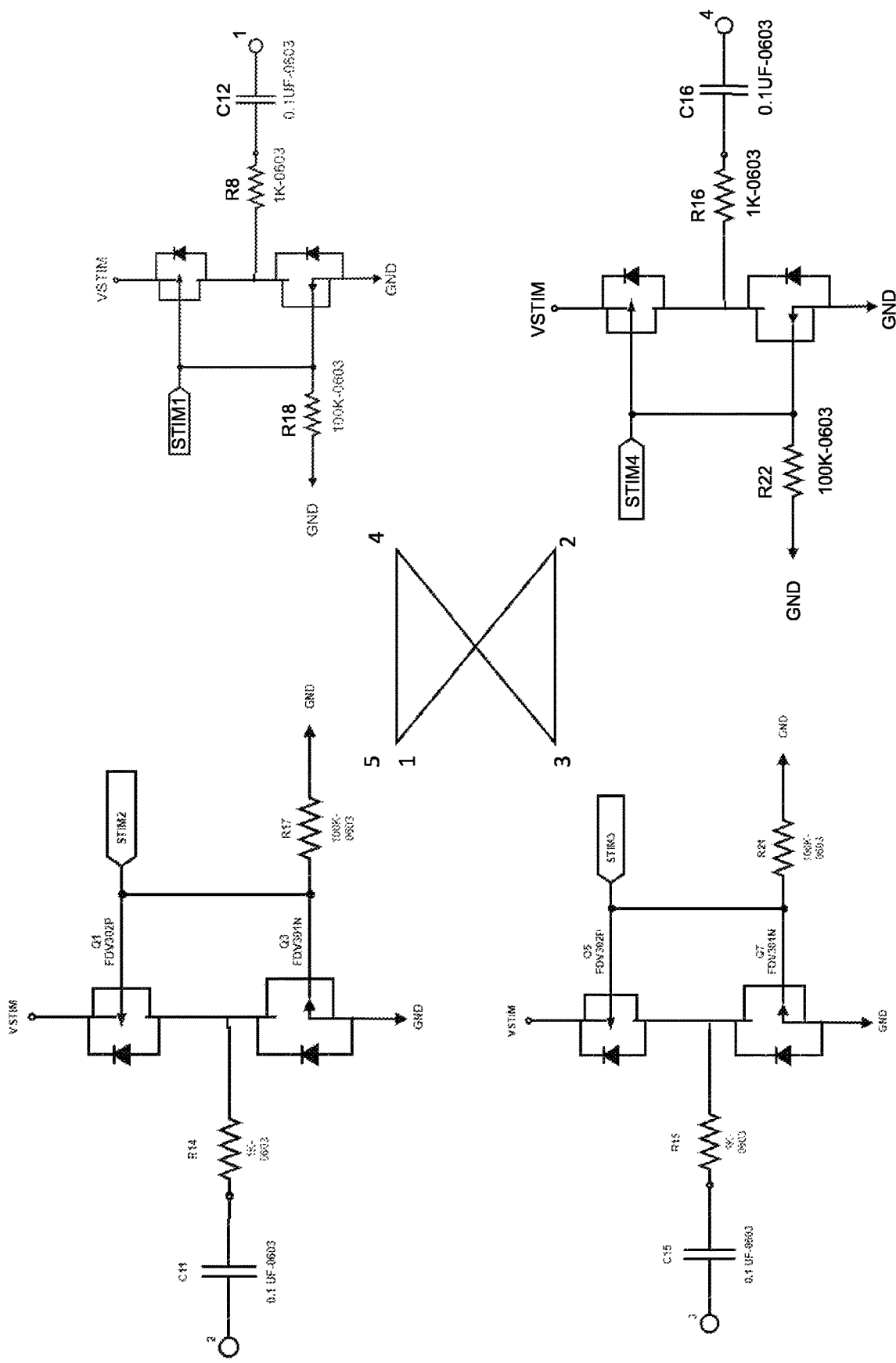
Figure 52:
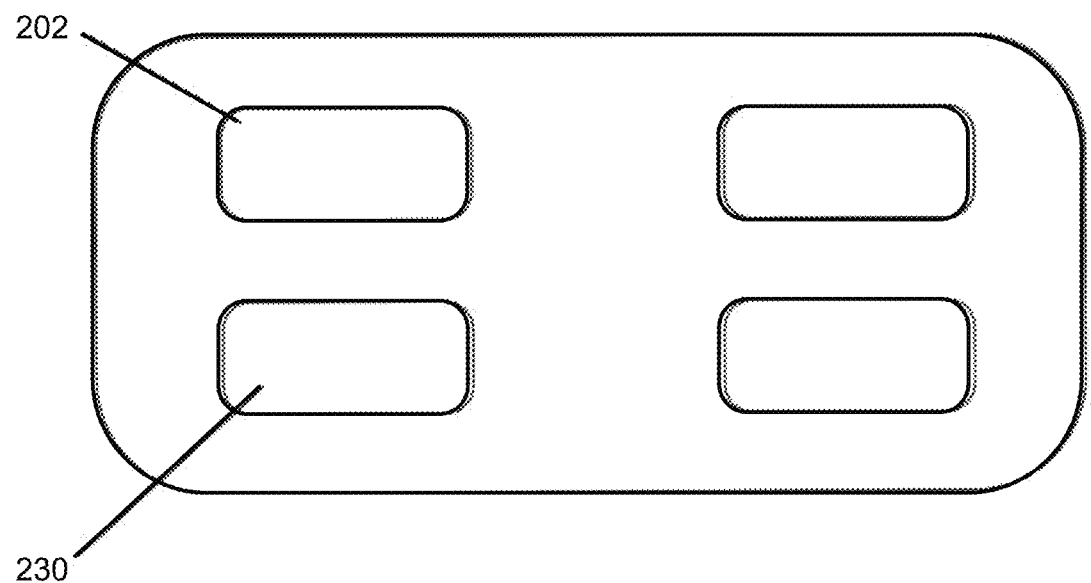
FIG. 52 is a perspective top view of hingeable sexual dysfunction treatment systems, including replaceable gel pads, according to embodiments of the present invention.

In another embodiment of the present invention, the housing 202 can comprise a molded flexible housing manufactured from a PVC, polyethylene or polyurethane material. As illustrated in FIG. 46, the housing 202 has an interior configured to hold the circuit board element 204 and the electrodes 230. The molded housing 202 can also include openings or recesses for holding the electrodes 230, sensors, switches 206, power supply 240, and other features that are in operative communication with the device 200.

In one example embodiment of the present invention, the electrode containment or wing portions 202a can have a thickness generally less than, greater than, or equal to a thickness of the central body portion 102b. The variation in the thickness of the electrode containment or wing portions 202a can aid in enabling their flexing with respect to the central body portion 202b. The housing 202 can also comprise one or more web portions 208 extending between and connecting the electrode containment wing portions 202a and the central body portion 202b. The web portion can have a thickness generally less than a thickness of the electrode containment portions 202a and the central body portion 202b to facilitate easier flexing of the electrode containment portions 202a.

Figure 45:
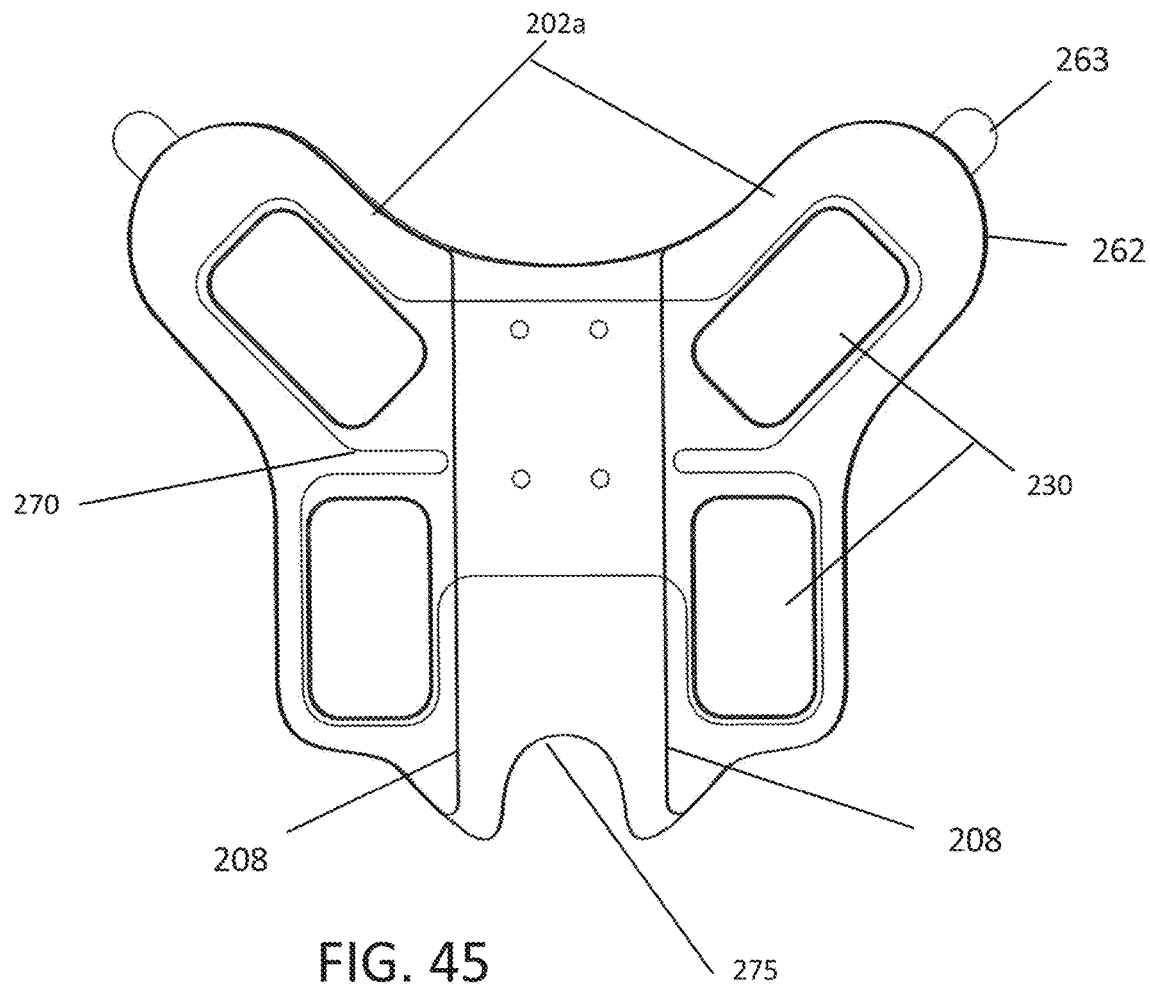
FIG. 45 is a top view of a hingeable sexual dysfunction treatment system with gel pads attached, according to embodiments of the present invention.

As illustrated in FIG. 45, the wing portions 202a of the housing 202 may include one or more notches or slits 270 extending therein or therethrough. The notches 270 may have a length extending generally perpendicular to a long axis of the housing 202. The notches 270 enable the housing 202, the wing portions 202a, and the electrodes 230 to move independently. This is of particular importance in the area of the perineum where the user's legs, genitals, and buttocks can each move independently. The combination of the notches 270 and the foldable areas 208 between the central body 202b and the wing portions 202a of the housing 202 creates a device 200 that is flexible and adaptable to the user's body and movements.

The device 200 also may include a recess 275 that extends into the housing 202 to accommodate the base of the scrotum. As illustrated in FIG. 45, the recess or channel 275 that extends generally into the central body portion 202b of the housing 202 to accommodate anatomy, such as the scrotum, when worn by a male user. In one embodiment, a portion of the housing 202 is trimmable to accommodate different anatomical structures and configurations. For instance, the recess 275 may comprise a trimmable material such that it can be trimmed by a user to create a custom fit. The housing 202 can have a wider adhering surface area to allow for improved adhesion to a user's skin. By having the ability to trim the housing 202 a user can leave some of the housing 202 untrimmed to increase adhesion.

Figure 28:
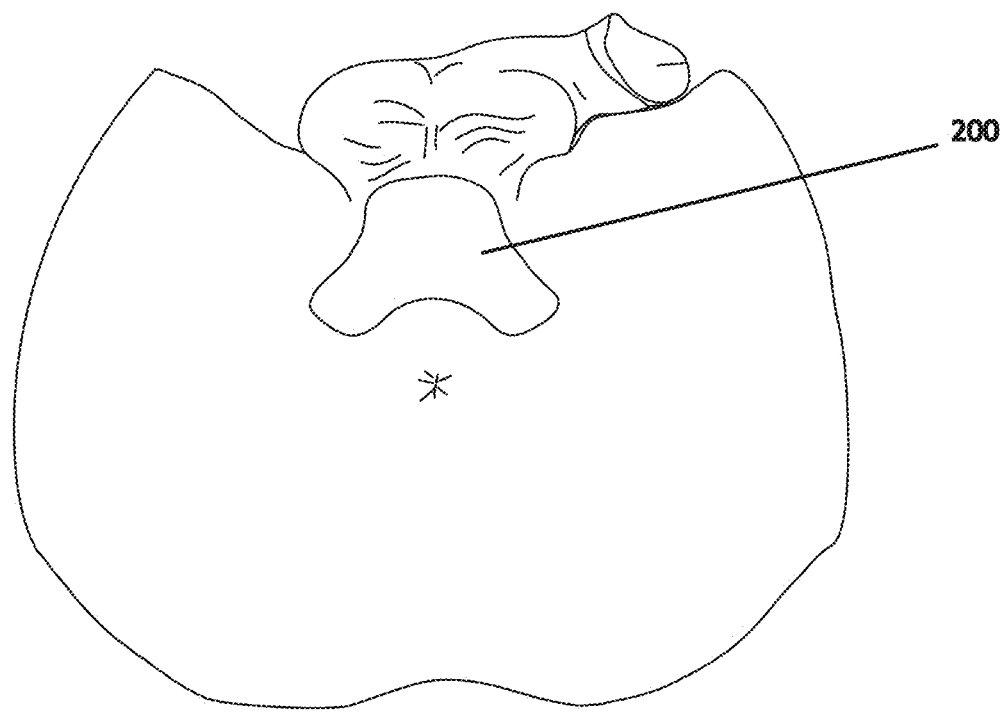
FIG. 28 is a view of the initial anatomical placement of a hingeable sexual dysfunction treatment system, according to embodiments of the present invention.
Figure 29:
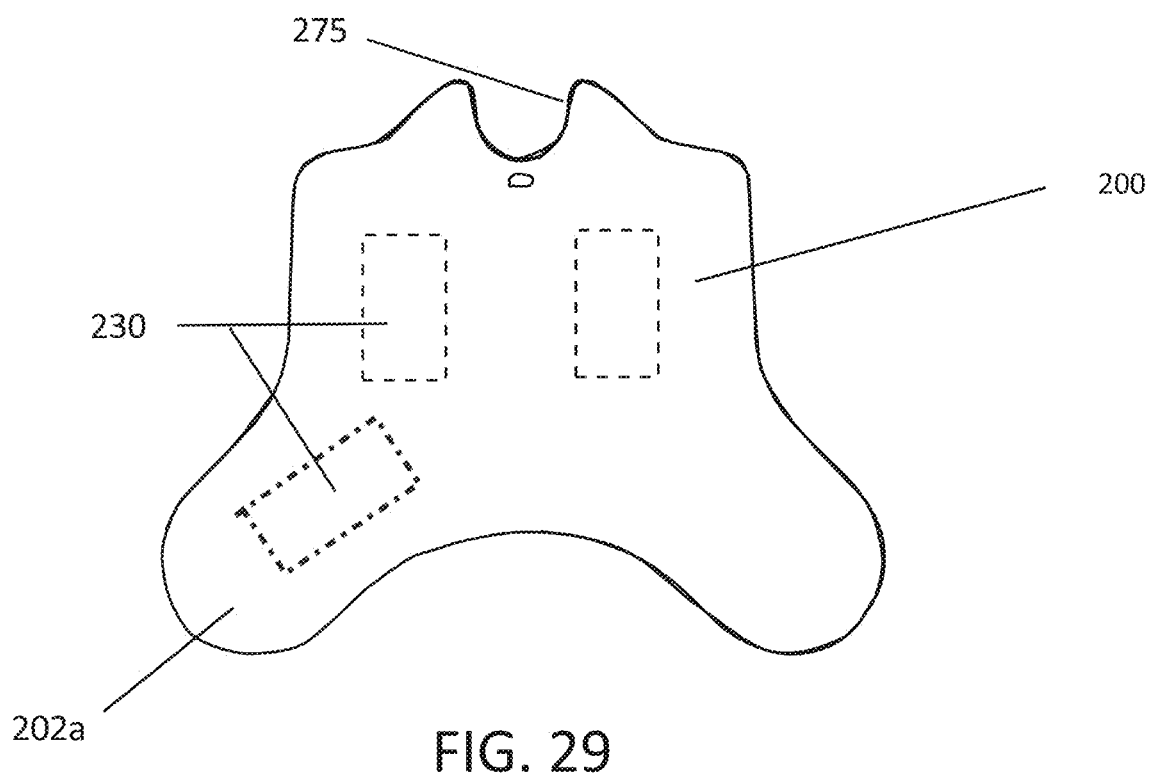
FIG. 29 is a back view of a hingeable sexual dysfunction treatment system, according to embodiments of the present invention.
Figure 30:
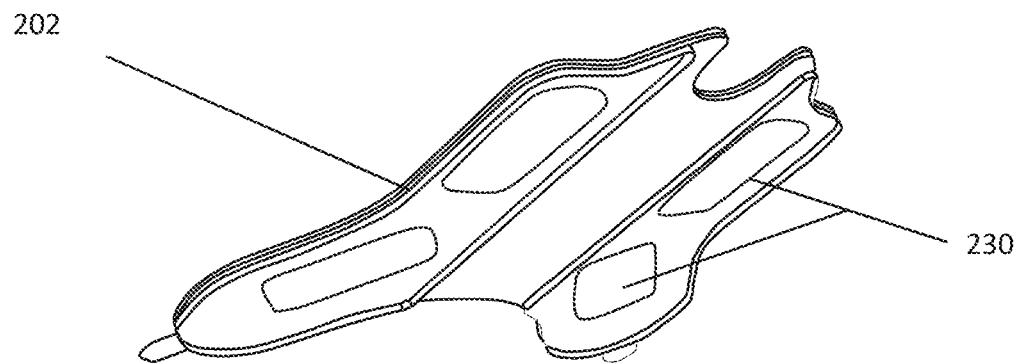
FIG. 30 a front perspective view of a hingeable sexual dysfunction treatment system, showing electrodes according to embodiments of the present invention.
Figure 31:
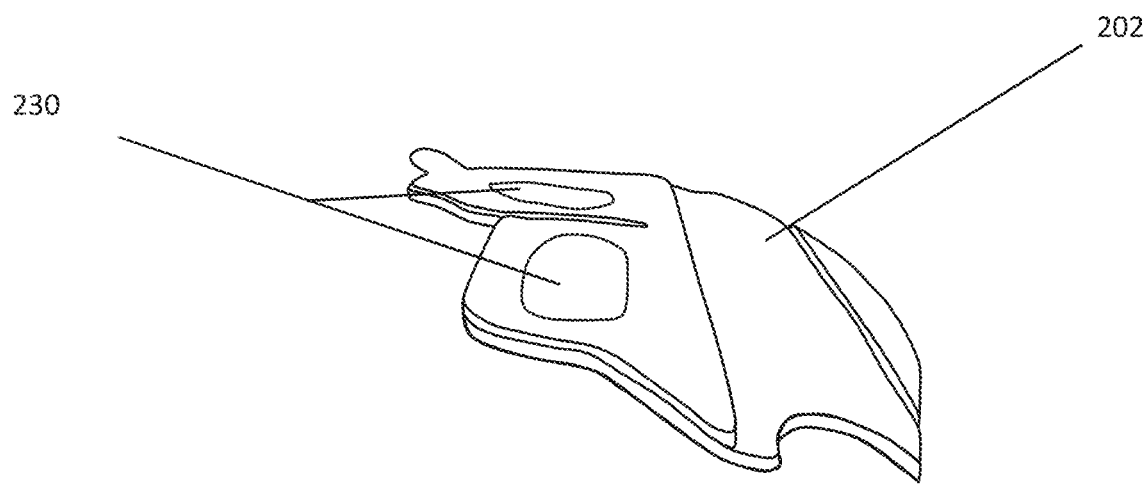
FIG. 31 is a top perspective view of a hingeable sexual dysfunction treatment system showing electrodes, according to embodiments of the present invention.
Figure 32:
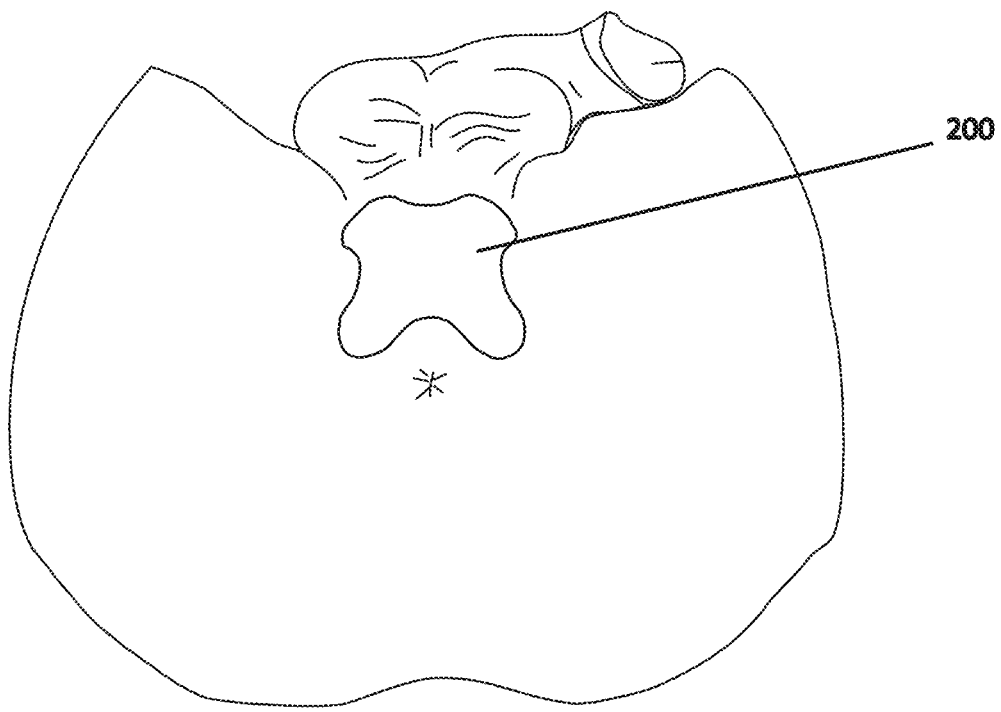
FIG. 32 is a view of an example anatomical placement of a hingeable sexual dysfunction treatment system, according to embodiments of the present invention.
Figure 33:
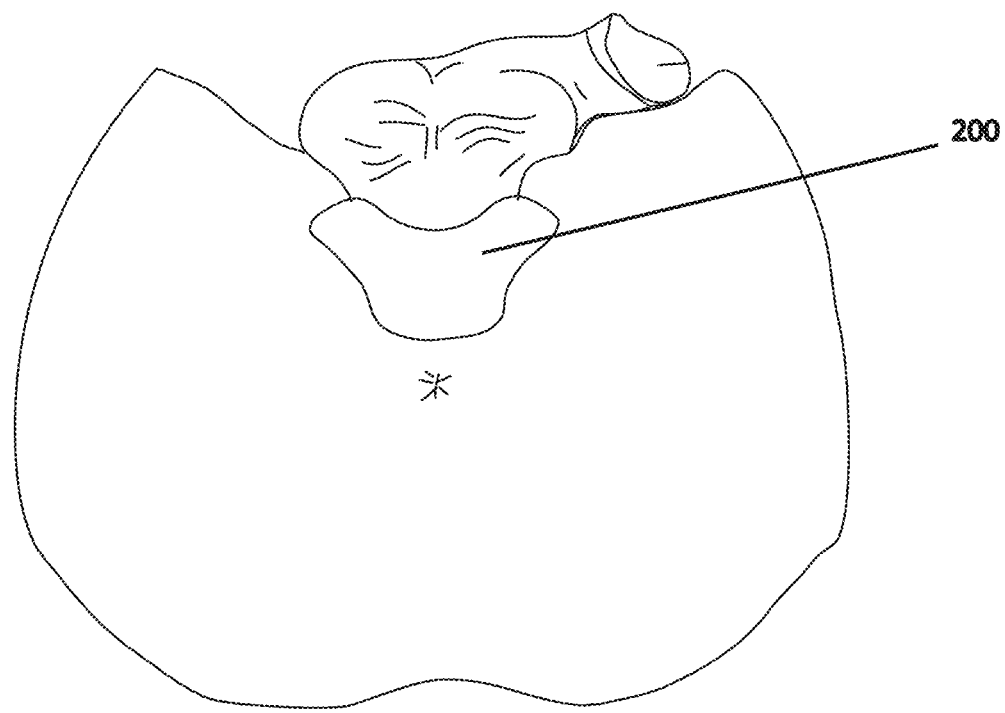
FIG. 33 is a view of an example anatomical placement of a hingeable sexual dysfunction treatment system, according to embodiments of the present invention.
Figure 34:
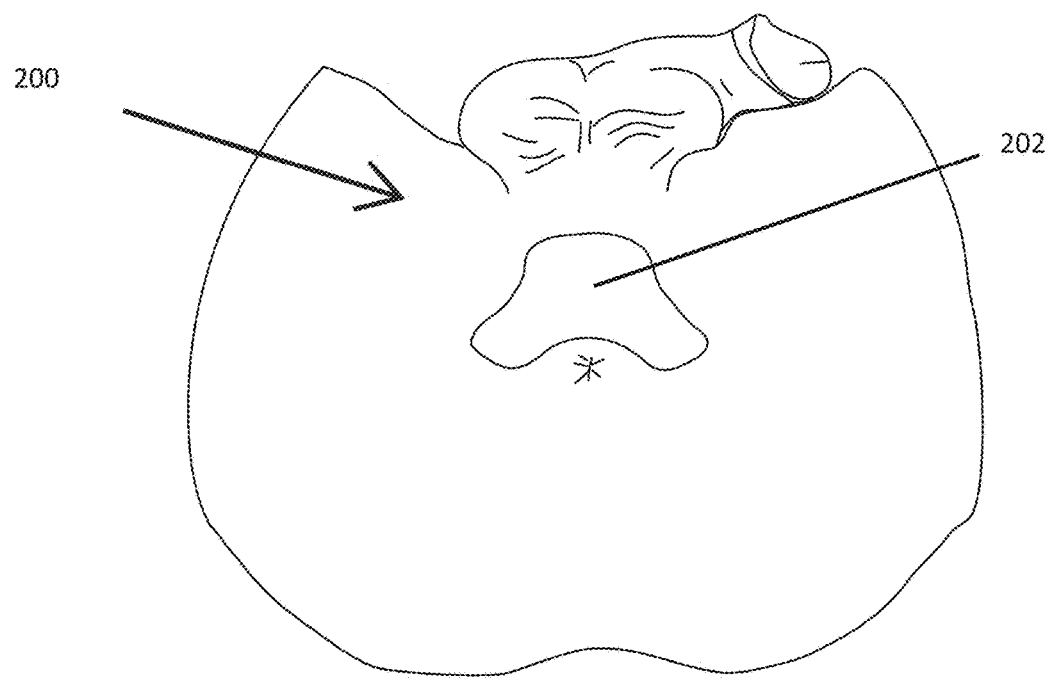
FIG. 34 is a view of an example anatomical placement of a hingeable sexual dysfunction treatment system, according to embodiments of the present invention.
Figure 35:
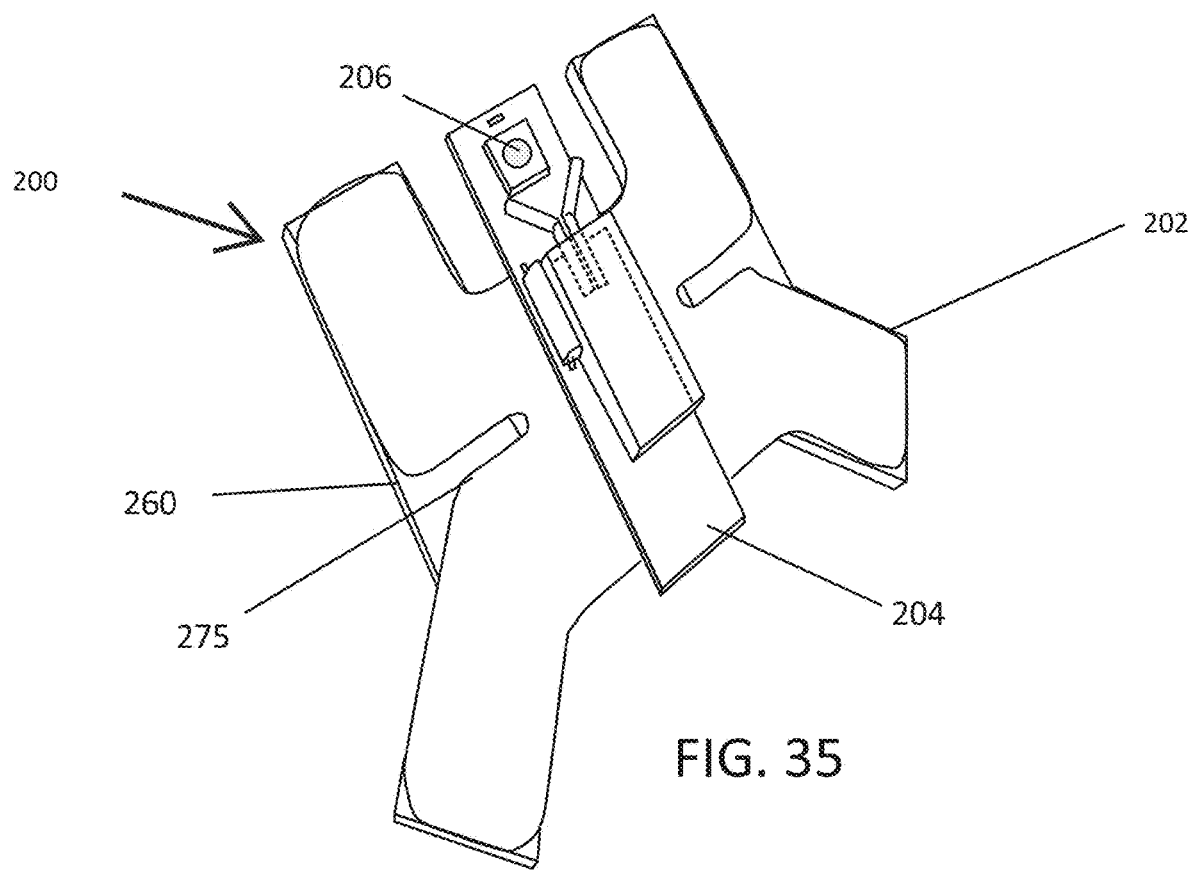
FIG. 35 is a bottom perspective view of a hingeable sexual dysfunction treatment system showing detachable power and control module, according to embodiments of the present invention.
Figure 36:
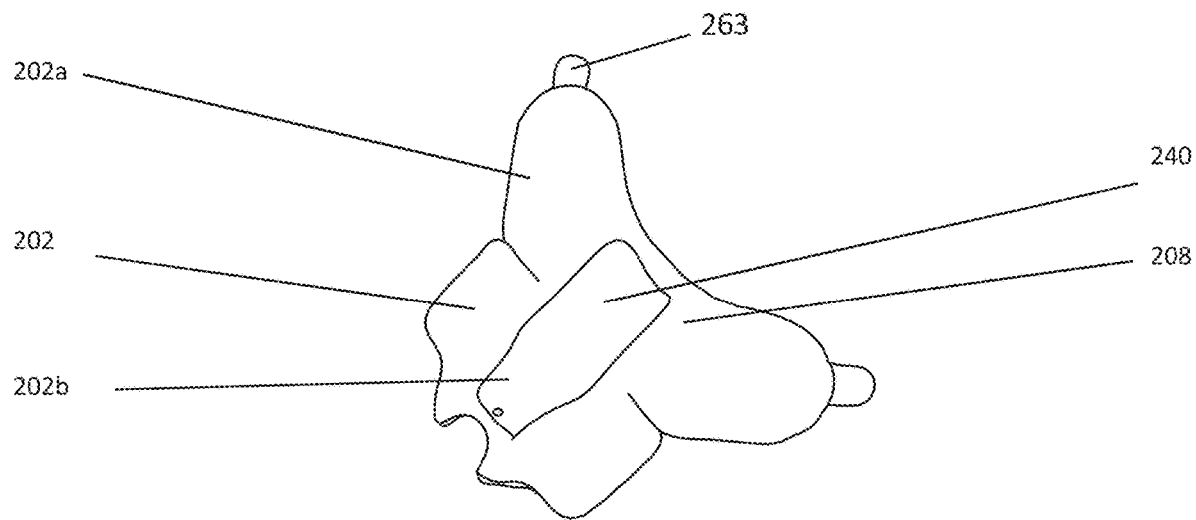
FIG. 36 is a bottom view of a hingeable sexual dysfunction treatment system, according to embodiments of the present invention.

In another embodiment of the invention, as illustrated in FIGS. 28 and 32 and 34, one or more electrodes 230 of the device 200 are positioned posteriorly toward the user's perineal region or anus. The design of the device 200, positions electrodes 230 near nerves enervating the anus and rectum. These nerves include the Inferior rectal nerves and the inferior hemorrhoidal nerves which branch from the pudendal nerve. The nerves near the perineal region also enervate the prostate. As these nerves and other nerves in the area are stimulated by the device 200 described herein, an intensification of ejaculation or orgasm can occur.

Figure 38:
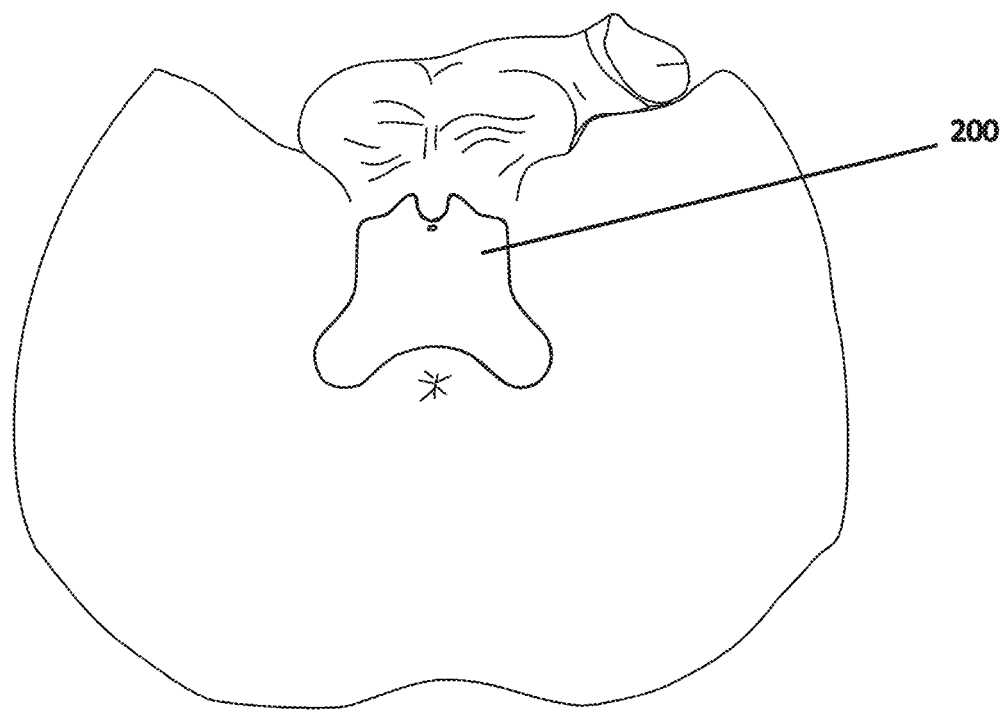
FIG. 38 a view of an example anatomical placement of a hingeable sexual dysfunction treatment system, according to embodiments of the present invention
Figure 39:
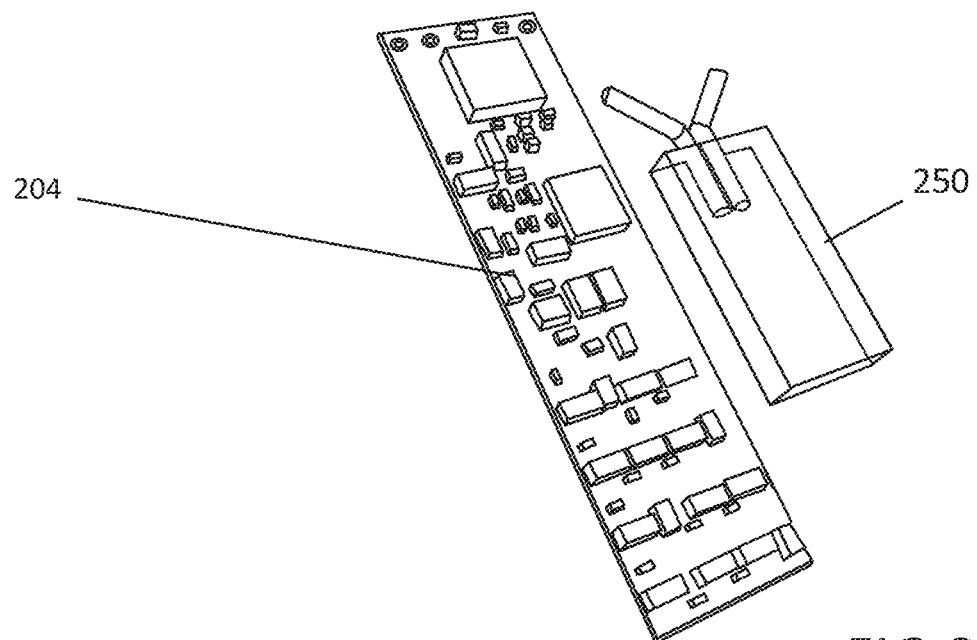
FIG. 39 is a top perspective view of a circuit board element for a hingeable sexual dysfunction treatment system with an attachable power supply and control module, according to embodiments of the present invention.

Referring to FIGS. 28 and 38, the device 200 is placed such that electrodes are positioned near the dorsal nerves and the rectal or anal nerves. The device 200 is able to stimulate both sets of nerves and is able to control timing of an orgasm and/or the intensification of the orgasm. Referring to FIG. 34, the device 200 is positioned closer to the anus. Further, the device 200 may include only two electrodes 230 positioned in the wing portions 202a proximate the anus. This configuration of the device 200 allows for stimulation of the nerves enervating the prostate and can cause an increase in the intensification of an orgasm. It is also contemplated herein to have a device 200 that only stimulates the dorsal or pudendal nerve top allow for control of the timing of an orgasm rather the intensification.

In operation, the device 200 provides non-uniform and changing effective electrical stimulation timing of pulses with varying effective voltages and/or frequencies to "confuse" nerves and receptors involved in the ejaculatory process while also stimulating the nerves near the perineal region and the prostate. The targeted neural network runs between the base of the penis, the perineal region, and the spinal cord, all of which are within the region of the perineum. This is the anatomical area closest to those nerves and receptors involved in the ejaculatory process. There are other excitable tissues in the region that may receive electrical stimuli as well via the device 200. The device 200 is placed transperineally, with the electrodes 230 crossing the plane of nerves running parallel with the urethra and the anus.

Similar to the other embodiments, the electrical stimulation of the device 200 is directed through the electrodes 230 using a non-uniform selection from one electrode to another. This stimulation pattern results in varying length pathways and a variance of time and physical distance for stimulations contacting those nerves and receptors. This results in an "ultra" neural stimulation at various times and directions within the ejaculatory neural network, thereby providing a varying of absolute and relative refractory time periods as well as their baseline resting membrane potential. Stimulations occur over varying parts of the refractory periods of the excitable cells in the perineal region, thereby resulting in neuromodulation of the ejaculatory process via neuro-confusion. This "ultra confusion" is imparted on the nerves and receptors, which promotes a modulation of nerve signal conduction, which results in time prolongation of ejaculation. Because the stimuli are constantly varying, there is a dramatic reduction or elimination of neurologic adaption to electrical signals, as well as a more effective neural modulation of the pathway. While the time to ejaculation is delayed the intensity of the ejaculation, once it occurs, is increased.

The device 200 can be controlled and adjusted with a remote or mobile device 150, such as a smartphone and executed mobile app, in operative wireless communication with the circuit board element 204. The mobile app can receive feedback, monitor operation, log device and treatment information and data, analyze device and treatment information and data, and the like. The mobile device 150 or controller 250 can be used and operated by the patient, the patient's partner, and other authorized third parties.

Conductive electrode gel pads 260 are provided for placement and adherence over the one or more of the electrodes 230 during use. A single gel pad 260 can cover a single electrode 230, or two adjacent electrodes 230. The gel pads 260 can be replaced between uses of the device 200. The housing 202 of the device 200 can include a raised ridge portion that extends about the electrode containment portions 202a and 202b. The raised ridge portion aids a user in positioning the gel pads 260 over the electrodes 230. A covering 262 can be provided to cover the gel pad 260 until use. The covering 262 can include a tab portion 263 that extends beyond the housing 202 to allow a user to easily grasp and remove the covering prior to use.

Similar to the schematic diagrams of FIGS. 26-27, embodiments of the device 200 include a touch sensor that is inside or on the housing 202 and activated by pressing on the flexible housing 202. The device 200 also includes a microcontroller, a stim wave generator, a power source 240, a plurality of stim drivers, and the plurality of electrodes 230. The power source 240 of the device 200, used to control the components of the device, can be rechargeable. As such, the device 200 can include a charging port or wireless charging technology. In another example embodiment of the present invention, the power source 240 can be charged by wireless transmission through the one or more electrodes 230. In this way, the one or more electrodes 230 are able to provide a dual function of providing treatment and charging the power source 240. The device 200 can include a wireless charger that is able to interface with a portion of the device, or one or more of its electrodes 230 to charge the power source 240.

Figure 53A:
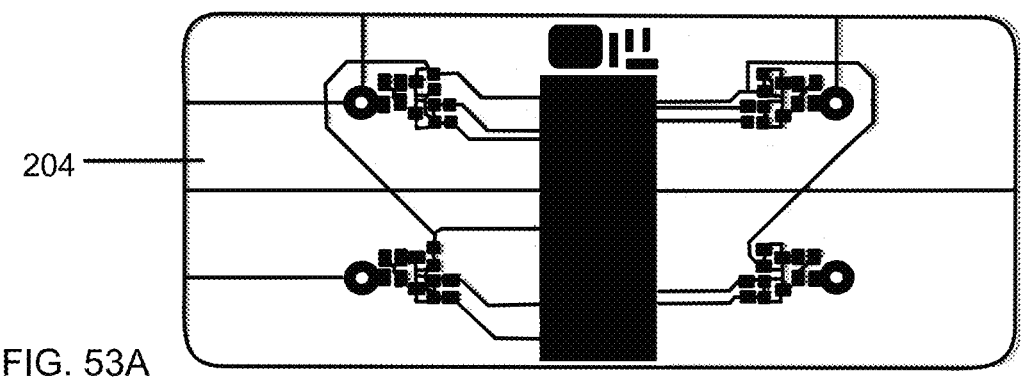
FIG. 53A is a top view of hingeable sexual dysfunction treatment systems illustrating an example circuitry configuration, according to embodiments of the present invention.
Figure 53B:
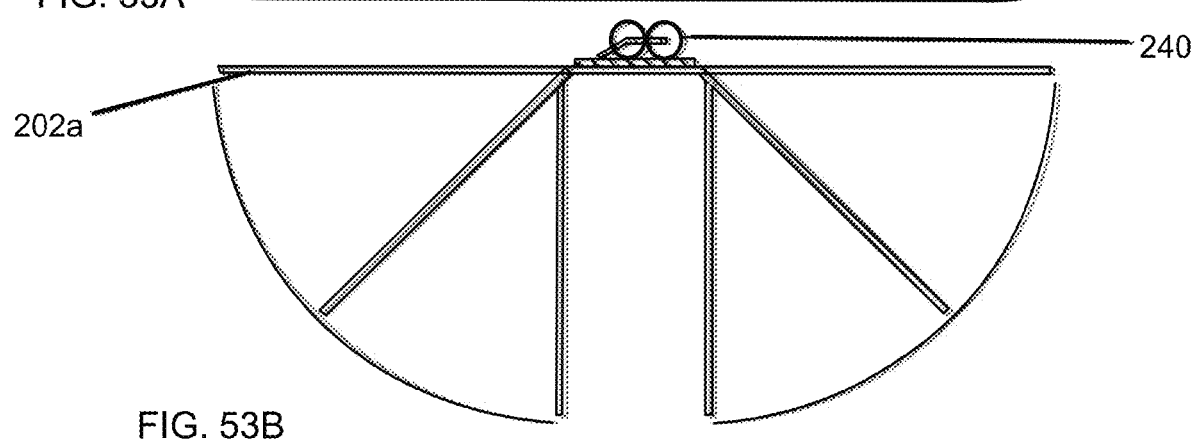
FIG. 53B is a front view of hingeable sexual dysfunction treatment systems illustrating example hinged positions, according to embodiments of the present invention.
Figure 54:
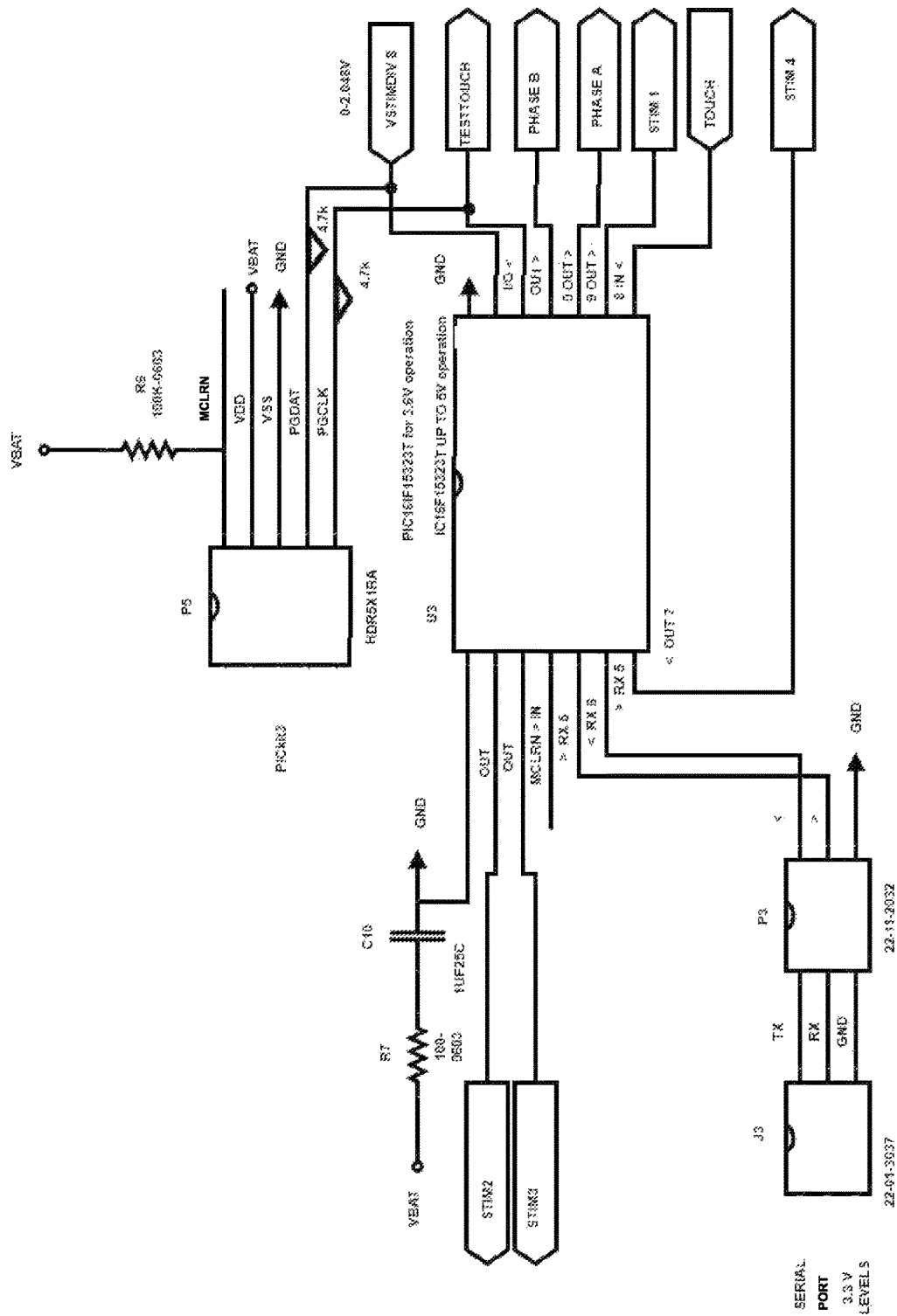
FIG. 54 is an example electronic schematics of a sexual dysfunction treatment system, according to example embodiments of the invention.

The flexibility of the housing 202 is illustrated in FIG. 53B, where it can be seen that the wing portions 202a of the housing 202 are able to flex and pivot from a generally flat orientation or configuration to a bent or 90 degree or greater configuration. While 0 to 90 degree flexibility is illustrated, the device 200 is also able to bend or flex greater than 90 degrees from its flat configuration.

The onboard power source 240 allows the device 200 to generate between one and four or more stim vectors through the electrodes 230 that vary in voltage and frequency. For example, the vector sequence can include the following pattern: electrode 1 to electrode 2; electrode 1 to electrode 3; electrode 4 to electrode 3, and electrode 4 to electrode 2. This pattern can be repeated or alternate between different patterns. A user selected voltage target changes the pulse frequency as well. Other effective therapeutic vector patterns and control adjustments can also be utilized without deviating from the spirit and scope of the present invention. For instance, the vector drives can be random or nearly random, the voltage, frequency and other vector patterns can be changed, a sequence or modulate voltage and/or frequency can be adjusted to obtain the highest level of neural confusion, voltage and frequency and applied modulations can be independently controlled, and stimulation and un-stimulation (or varied with a pattern) can occur that results in triggering the final ejaculation event via user control.

The device 200 is also able to have varying stimulation patterns between the electrodes 230 near the base of the penis and those near the perineal region. The result is customized stimulation to control the delay of ejaculation and the intensity of the eventual ejaculation or orgasm.

The device 200, similar to the other embodiments, is able to vary any of its parameters to aid in the "ultra confusion" of targeted nerves and pathways. The following are some examples of device parameters that can be varied:
Voltage and/or current levels
Voltage and/or current duration
Stim delivery frequency or period
Energy delivered
Impedance
Applied stim vector pattern and sequencing
Modulation of one or more of the above variables The present invention can also include one or more sensors that are able to sense an approaching ejaculatory event and then alter or modulate one of the above device parameters in order to provide effective stimulation therapy to delay the ejaculation. In one example embodiment, the electrodes 230 are also capable of acting as a sensor. In this embodiment, the electrodes 230 are able to sense a change in the skin potential that signals an approaching ejaculatory event. Other sensors may also be employed. For instance, stretch sensors can be used to detect the peristaltic waves or contractions of the penis or anus. These contractions typically precede and coincide with an ejaculation. When a peristaltic contraction is detected the device 200 can modulate the therapy, thereby confusing the nerves until the peristaltic contractions stop. This process can be repeated until the user or their partner desires the ejaculatory event to occur, at which point they can turn off or reduce the therapy being delivered.

Sensors for detecting physiological and device parameters can include accelerometers, stretch sensors, impedance sensor—(may change nearing the event or in relation to other factors), temperature sensor, motion sensors (1, 2 and 3D accelerometers for force, distance, rep rate, etc.), photosensors with or without LED light source (e.g., to sense heart rate, blood flow rate), and/or pressure sensors (e.g., measure blood pressure or changes in penis diameter). Other sensors and detection devices are also considered to be within the spirit and scope of the invention.

Another advantage of stimulating the nerves proximate the anus and prostate is a marked increase in the girth of the penis during ejaculation. This works by stimulating the muscles in the perineal area to include the prostate muscles. The benefits of ejaculation intensification include greater sexual pleasure, satisfaction and performance. In addition, the effect may increase ejaculate volume which could be of benefit in men who suffer from infertility issues. As men age, the neuromuscular response is decreased which could lead to less intense ejaculations. By using neurostimulation, ejaculation intensity could be restored in those individuals who may have had a decrease in ejaculation intensity.

In another embodiment of the present invention, the power supply 240, or the power supply 240 and the circuitry elements/components 204 may be housed separately from but removably connectable to the patch 260 to allow for the patch 260 to be replaced after one or more uses but allowing the power supply 240/circuitry 204 to be resused. This embodiment of the present invention reduces costs for consumers while also reducing the amount of waste entering the environment.

While the invention has been described in connection with what is presently considered to be the most practical and preferred embodiments, it will be apparent to those of ordinary skill in the art that the invention is not to be limited to the disclosed embodiments. It will be readily apparent to those of ordinary skill in the art that many modifications and equivalent arrangements can be made thereof without departing from the spirit and scope of the present disclosure, such scope to be accorded the broadest interpretation of the appended claims so as to encompass all equivalent structures and products. Moreover, features or aspects of various example embodiments may be mixed and matched (even if such combination is not explicitly described herein) without departing from the scope of the invention.

What is claimed is:

1. A system for altering an approaching sexual event, the system configured to be removably placed anywhere on a user's body between a sex organ and an anus, the system comprising:
   a patch configured to be removably placed on a user, the patch comprising:
     a central body portion;
     first and second electrode wing portions operatively coupled to the central body portion by first and second hinge portions, wherein the first and second electrode wing portions are pivotally displaceable about the central body portion at the first and second hinge portions;
     circuitry elements; and
     at least first and second electrodes being associated with the first and second electrode wing portions respectively and in operative communication with the circuitry elements to provide electrical stimulation to the user;
   wherein the at least first and second electrodes further include third and fourth electrodes that are configured to be positionable proximate to the anus and are adapted to stimulate nerves of a prostate to increase an intensity of an ejaculatory event.

2. The system of claim 1, wherein the patch further includes a sensor configured to sense an approaching ejaculatory event.

3. The system of claim 2, wherein at least the first and second electrodes are positionable proximate to the sex organ and are adapted to stimulate pudendal nerves to delay an ejaculatory event.

4. The system of claim 2, wherein the sensor alters the electrical stimulation among the at least first, second, third and fourth electrodes upon sensing an ejaculatory event.

5. The system of claim 1, further comprising a wireless remote controller in operative communication with the circuitry elements to control a stimulation characteristic.

6. The system of claim 5, wherein the stimulation characteristic comprises at least one of intensity, time, period, and pattern.

7. The system of claim 5, wherein wireless the remote controller comprises a mobile device running a mobile app.

8. The system of claim 1, wherein the patch further comprises a switch configured to receive manual manipulation.

9. The system of claim 8, wherein the switch is configured to adjust stimulation intensity to the at least the first and second electrodes.

10. A system for intensifying an approaching sexual event, the system configured to be removably placed anywhere on a user's body between a sex organ and an anus, the system comprising:
    a patch configured to be removably placed on a user, the patch comprising:
      a central body portion;
      first and second electrode wing portions operatively coupled to the central body portion by first and second hinge portions, wherein the first and second electrode wing portions are pivotally displaceable about the central body portion at the first and second hinge portions;
      circuitry elements; and
      at least first and second electrodes being associated with the first and second electrode wing portions respectively and in operative communication with the circuitry elements to provide electrical stimulation to the user;
    wherein the first and second hinge portions include first and second living hinges extending longitudinally along first and second sides of the central body portion, wherein the first and second hinge portions have a thickness generally less than a thickness of the first and second wing portions.

11. A system for altering an approaching ejaculation event, the system configured to be removably placed anywhere on a user's body between a sex organ and an anus, the system comprising:
    a flexible patch configured to be removably placed on a user, the flexible patch comprising:
      a central body portion;
      a plurality of electrode wing portions operatively coupled to portions of the central body portion by at least one hinge portion extending therebetween, wherein the plurality of electrode wing portions are pivotally displaceable at least about the central body portion;
      circuitry elements operatively disposed on a portion of the central body portion;
      at least one electrode being associated with each of the plurality of electrode wing portions and each at least one electrode being in operative communication with the circuitry elements to provide electrical stimulation to the user; and
    wherein each of the electrode wing portions is configured to move independently of each other and the central body portion during use;
    wherein at least one of the electrodes are configured to be positionable proximate to the anus and configured to stimulate nerves of a prostate in order to increase an intensity of an ejaculatory event.

12. The system of claim 11, wherein the plurality of electrode wing portions is further defined by at least one notch extending between a pair of the plurality of electrode wing portions and generally perpendicular to a long axis of the central body portion.

13. The system of claim 11, further comprising a wireless remote controller in operative communication with the circuitry elements to control the electrical stimulation.

14. The system of claim 13, wherein the wireless remote controller comprises a remote mobile device in wireless operative communication with the circuitry elements.

15. The system of claim 13, further comprising a power supply configured to be removably connectable to and in operative communication with the circuitry elements.

16. The system of claim 11, wherein the flexible patch further comprises a switch in operative communication with the circuitry elements and configured to receive manual input.

17. The system of claim 16, wherein the switch is configured to receive manual input for adjusting the stimulation pattern of the at least one electrode of each of the electrode wing portions.

18. The system of claim 11, wherein the at least one hinge portion extends longitudinally along first and second sides of the central body portion and has a thickness generally less than at least the plurality of electrode wing portions.

19. The system of claim 11, wherein at least one of the electrodes is positionable proximate to the sex organ and configured to stimulate pudendal nerves in order to delay an ejaculatory event.

20. The system of claim 11, wherein the patch includes at least one sensor configured to sense an ejaculatory event and to alter the electrical stimulation.

\* \* \* \* \*